US006383745B1

(12) United States Patent
Rather

(10) Patent No.: US 6,383,745 B1
(45) Date of Patent: *May 7, 2002

(54) METHODS OF SCREENING FOR ANTI-MICROBIAL UTILIZING AARC AND COMPOSITIONS THEREOF

(75) Inventor: Philip N. Rather, Cleveland Heights, OH (US)

(73) Assignee: Case Western Reserve University, Cleveland, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/170,187

(22) Filed: Oct. 13, 1998

Related U.S. Application Data

(62) Division of application No. 08/827,190, filed on Mar. 27, 1997, now Pat. No. 5,858,367.

(51) Int. Cl.[7] .................................................. C12Q 1/68
(52) U.S. Cl. ................................ 435/6; 435/32; 435/4; 435/29; 435/69.1; 435/69.7; 435/69.8; 435/243; 435/252.3
(58) Field of Search .......................... 435/6, 69.8, 32, 435/29, 69.1, 69.7, 243, 252.3; 424/190.1; 536/23.1, 23.7, 24.32

(56) References Cited

U.S. PATENT DOCUMENTS

| 4,526,888 A | * | 7/1985 | Williams et al. ............... 514/12 |
| 4,683,195 A | | 7/1987 | Mullis et al. .................... 435/6 |
| 4,683,202 A | | 7/1987 | Mullis ........................... 435/91 |

OTHER PUBLICATIONS

Tenover et al. (1996) "Reasons for the Emergence of Antibiotic Resistance," *Am. J. Med. Sci.* 311:9–16.
Tenover and Hughes (1996) "The Challenges of Emerging Infectious Diseases, Developmental and Spread of Multiply–Resistant Bacterial Pathogens," *JAMA* 275:300–4.
Trieu–Cuot et al. (1985) "In vivo transfer of genetic information between Gram–positive and Gram–negative bacteria," *EMBO J.* 4:3583–3587.
Maniatis et al. (1987) "Regulation of Inducible and Tissue–Specific Gene Expression," *Science* 236:1237–1244.
Sambrook et al. (1989) *Molecular Cloning: A Laboratory Manual*, 2nd ed., Cold Spring Harbor Laboratory Press, NY pp. 16.7–16.8.
Sambrook et al. (1989) *Molecular Cloning: A Laboratory Manual*, 2nd ed., Cold Spring Harbor Press, NY, pp 9.31–9.58.
Sambrook et al. (1989) *Molecular Cloning: A Laboratory Manual*, 2nd ed., Cold Spring Harbor Press, NY, pp. 7.39–7.52.

Finegold and Martin (1982) Diagnostic Microbiology, 6th Ed., CV Mosby St. Louis, pp. 13–15.
Hawkey (1984) "*Providencia stuartii*: a review of a multiply antibiotic–resistant bacterium,"*J. of Antimicrob. Chemo.* 13:209–226.
Penner et al. (1982) "Species Differences in Susceptibilities of Proteeae spp. to Six Cephalosporins and Three Aminoglycosides," *Antimicrobial Agents and Chemo.* 22:218–221.
Hawkey et al. (1983) "Comparative In Vitro Activity of Semisynthetic Penicillins Against Proteeae," *Antimicrobial Agents and Chemo.* 23:619–621.
Rather et al. (1993) "Characterization and Transcriptional Regulation of the 2'–N–Acetyltransferase Gene from *Providencia stuartii*," *J. Bacteriol.* 175:6492–6498.
Chevereau et al. (1974) "Aminoglycoside Resistance in Bacteria Mediated by Gentamicin Acetyltransferase II, an Enzyme Modifying the 2'–Amino Group of Aminoglycoside Antibiotics," *Biochemistry* 13:598–603.
Yamaguchi et al. (1974) "A 2'–N–Acetylating Enzyme of Aminoglycosides," *J. Antibiotics* 27:507–515.
Macinga et al. (1996) "aarD, a *Providencia stuartii* homologue of cydD: role in 2'–N–acetyltransferase expression, cell morphology and growth in the presence of an extracellular factor," *Mol. Microbiol.* 19:511–520.
Macinga et al. (1995) "Identification and Analysis of aarP, a Transcriptional Activator of the 2'–N–Acetyltransferase in *Providencia stuartii*," *J. Bacteriol.* 177:3407–3413.
Baker et al. (1992) "Sequence and characterization of the gcpE gene of *Escherichia coli*," *FEMS Microbiology Letters* 92:175–180.
Eisenbeis and Parker (1981) "Strains of *Escherichia coli* Carrying the Structural Gene for Histidyl–tRNA Synthetase on a High Copy–Number Plasmid," *Mol. Gen. Genet.* 183:115–122.
Barany (1991) "Genetic disease detection and DNA amplification using cloned thermostable ligase," *Proc. Natl. Acad. Sci.* 88:189.

(List continued on next page.)

Primary Examiner—Jennifer E. Graser
(74) Attorney, Agent, or Firm—Medlen & Carroll, LLP

(57) ABSTRACT

The present invention provides an oligonucleotide (aarC) which encodes a novel bacterial polypeptide (AarC) that is essential for the viability of bacteria. The invention provides recombinant expression vectors comprising the nucleotide sequence encoding AarC, as well as host cells containing these expression vectors. Further provided herein are methods for screening bacteria which contain aarC or variants or homologs thereof. Also provided are methods for using the aarC oligonucleotide sequence to screen antimicrobials which target AarC activity in gram negative and gram positive bacteria. Additionally, the invention provides for the use of aarC in diagnostic assays which utilize the aarC oligonucleotide to hybridize with nucleic acid sequences encoding AarC as well as with AarC mRNA. The invention further describes monoclonal and polyclonal AarC antibodies and their use in diagnostic assays for the detection of bacteria which express AarC.

11 Claims, 14 Drawing Sheets

OTHER PUBLICATIONS

Barany (1991) "The Ligase Chain Reaction in a PCR World," *PCR Methods and Applic.* 1:5.

Wu and Wallace (1989) "The Ligation Amplification Reaction (LAR)—Amplification of Specific DNA Sequences Using Sequential Rounds of Template–Dependent Ligation," *Genomics* 4:560–569.

Snyder et al. (1986) "Basic Concepts of Chemotherapy," in *Modern Pharmacology*, 2d Ed., C. R. Craig and R. E. Stitzel, (eds.), Little, Brown and Company, Boston, pp. 631–640.

Conte et al. (1988) "Section IV, Antibiotic Susceptibilities," in *Manual of Antibiotics and Infectious Diseases*, 6th Ed., Lea and Febiger, Philadelphia, pp. 135–152.

Woods (1995) "In Vitro Testing of Antimicrobial Agents," *Infect. Dis. Clin. North. Am.* 9(3):463–481.

Moseley et al. (1980) "Detection of Enterotoxigenic *Escherichia coli* by DNA Colony Hybridization", *J. Infect. Dis.* 142:892–898.

Perine et al. (1985) "Evaluation of a DNA–Hybridization Method for Detection of African and Asian Strains of *Neisseria gonorrhoeae* in Men with Urethritis," *J. Infect. Diseases* 152(1):59–63.

Gootz et al. (1985) "Comparison of Three DNA Hybridization Methods for Detection of the Aminoglycodside 2"–O–Adenylytransferase Gene in Clinical Bacterial Isolates," *Antimicrob. Agents and Chemother.* 28(1):69–73.

Köhler and Milstein (1975) "Continuous cultures of fused cells secreting antibody of predefined specificity," *Nature* 256:495–497.

Kozbor et al. (1983) "The production of monoclonal antibodies from human lymphocytes," *Immunol Today* 4:72–79.

Cote et al. (1983) "Generation of human monoclonal antibodies reactive with cellular antigens," *Proc. Natl. Acad. Sci.* 80:2026–2030.

Cole et al. (1985) "The EBV–Hybridoma Technique and Its Application to Human Lung Cancer," in *Monoclonal Antibodies and Cancer Therapy*, Alan R Liss Inc, New York NY, pp. 77–96.

Miller et al. (1988) "A Novel Suicide Vector and Its Use in Construction of Insertion Mutations: Osmoregulation of Outer Membrane Proteins and Virulence Determinants in *Vibrio cholerae* Requires toxR," *J. Bacteriol.* 170:2575–2583.

Chang et al. (1978) "Construction and Characterization of Amplifiable Multicopy DNA Cloning Vehicles Derived from the P15A Cryptic Miniplasmid," *J. Bacteriol.* 134:1141–1156.

Kaniga et al. (1991) "A wide–host–range suicide vector for improving reverse genetics in Gram–negative bacteria: inactivation of the blaA gene of *Yersinia enterocolitica*," *Gene* 109:137–141.

Payie et al. (1995) "Contribution of Gentamicin 2'–N–Acetyltransferase to the O Acetylation of Peptidoglycan in *Providencia stuartii*," *J. Bacteriol.* 177:4303–4310.

Rather and Orosz (1994) "Characterization of aarA, a Pleiotrophic Negative Regulator of the 2'–N–Acetyltransferase in *Providencia startii*," *J. Bacteriol.* 176:5140–5144.

Farinha et al. (1990) "Construction of Broad–Host–Range Plasmid Vectors for Easy Visible Selection and Analysis of Promoters," *J. Bacteriol.* 172:3496–3499.

Miller (1972) "The Role of Cell Surface Oligosaccharide Units in Blastogenic Stimulation of Human Lymphocytes," Cold Spring Harbor Laboratory, Cold Spring Harbor, NY, p. 30.

Fleischmann et al. (1995) "Whole–Genome Random Sequencing and Assembly of *Haemophilus influenzae* Rd," *Science* 269:496–512.

*Antibodies: A Laboratory Manual* (1988) Harlow and Lane, Eds. Cold Spring Harbor Laboratory Press, Cold Spring Harbor, NY, p. 144.

Acar (1985) "Problems and Changing Patterns of Resistance with Gram–Negative Bacteria," *Rev. Infect. Diseases* 7:S545–S551.

Fukaya et al. (1993) "The aarC Gene Responsible for Acetic Acid Assimilation Confers Acetic Acid Resistance on *Acetobacter aceti*," *J. Ferm. and Bioeng.* 76:270–275.

Murray (1992) "Problems and Dilemmas of Antimicrobial Resistance," *Pharmacotherapy* 12:86S–93S.

Tenover (1986) "Studies of Antimicrobial Resistance Genes Using DNA Probes," *Antimicro. Agents and Chemo.* 29:721–725.

Tenover (1989) "DNA Probes for Antimicrobial Susceptibility Testing," *Clin. in Lab. Med.* 9:341–347.

Thornsberry (1995) "Trends in Antimicrobial Resistance Among Today's bacterial Pathogens," *Pharmacotherapy* 15:3S–8S.

Thornsberry (1996) "Emerging Resistance in Clinically Important Gram–Positive Cocci," *West J. Med.* 164:28–32.

Washington (1989) "In Vitro Testing of Antimicrobial Agents," *Infec. Dis. Clin. N. Amer.* 3:375–387.

Wexler (1993) "Susceptibility Testing of Anaerobic Bacteria—The State of the Art," *Clin. Infec. Dis.* 16:S328–S333.

Zak et al. (1990) "Remarks on the Screening of Antibiotics for Antibacterial Activity," *Eur. J. Clin. Microbiol. Infect. Dis.* 9:462–465.

Fleischmann et al., "Protein E (gpcE) homolog—Haemophilus influenzae (strain Rd KW20)," PIR51 database, accession No. H64063 (Aug. 18, 1995).

Murray et al., *Manual of Clinical Microbiology* "Antimicrobial Susceptibility Testing: General Considerations," 6th ed., ASM Press, Washington, D.C. 19950 pp. 1277–1280 (1995).

Woods et al. 1995. Infect. Dis Clin. N. America. 9(3): 463–481.*

Hawkey et al. Antimicrob. Agents & Chemoth. 1983. 23(4): 619–621.*

Macinga et al. 1996. 19(3): 511–520.*

Kunst et al. 1997. Nature 390(6657): 249–256.*

Baker et al. 1992. FEMS Microbiology Letters. 94: 175–180.*

* cited by examiner

Figure 2

```
TTAAAAATACCTGAAGCATAAAGTCACAAATTAAGAAGACGCAAACTGTATCCTAAAACTAGAATTGTGATAGTTTGCAG 80
TTTGCGTTTTTGTGTATAGTGGTCATCGAAGCAATGATTATCAACTACACAACAGTCTTTAAGAGCACATGGATGTCCAG 160
AGAGTAAAATTAAAATGCATAATGAATCACCGATAAAAAGACGTAAATCCACCCGAATTTATGTAGGTAACGTGCCTATT 240
                  M  H  N  E  S  P  I  K  R  R  K  S  T  R  I  Y  V  G  N  V  P  I
GGCGATGGTGCTCCCATTGCTGTCCAATCTATGACGAATACGCGCACGACGGATGTTGAAGCCACTGTGCGGCAAATCCA 320
  G  D  G  A  P  I  A  V  Q  S  M  T  N  T  R  T  T  D  V  E  A  T  V  R  Q  I  Q
ATCACTTGAGCGTGTAGGTGTTGATATCGTCCGCGTGTCTGTTCCTACGATGGATGCAGCAGAAGCCTTTAAATTAATTA 400
  I  T  L  E  R  V  G  V  D  I  V  R  V  S  V  P  T  M  D  A  A  E  A  F  K  L  I
AGCAGCGCGTGAATGTGCCATTGGTTGCGGATATTCACTTTGACTACCGTATCGCGATGAAAGTGGCTGAATATGGTGTT 480
  S  S  R  V  N  V  P  L  V  A  D  I  H  F  D  Y  R  I  A  M  K  V  A  E  Y  G  V
GACTGCCTACGAATTAACCCCAGGTAATATCGGCAGTGAAGAGCGTATTCGCCAAGTCGTTGATAGTGCTCGTCATCACAA 560
  D  C  L  R  I  N  P  G  N  I  G  S  E  E  R  I  R  Q  V  V  D  S  A  R  H  H  N
CATTCCTATCCGTATAGGGCTCAATGGCGGGTCACTGGAAAAAGATATCCAAGAAAAATACGGTGAGCCAACACCTGAAG 640
  I  P  I  R  I  G  V  N  G  G  S  L  E  K  D  I  Q  E  K  Y  G  E  P  T  P  E
CATTGGTTGAATCAGCAATGCGACATGTTGATATCTTGGACAGGCTGAATTTCGATCAGTTCAAGGTCAGTGTTAAAGCG 720
  A  L  V  E  S  A  M  R  H  V  D  I  L  D  R  L  N  F  D  Q  F  K  V  S  V  K  A
TCGGATGTCTTTCTTGCCGTCGGCTCTTATCGTTTATTGGCGCAAAAAATTGATCAACCACTTCACCTCGGTATTACAGA 800
  S  D  V  F  L  A  V  G  S  Y  R  L  L  A  Q  K  I  D  Q  P  L  H  L  G  I  T  E
AGCGGGTGGGGCTCGTTCTGGTTCAGTGAAATCAGCAATTGGTCTTGGTATGTTGTTGGCTGAAGGTATCGGCGATACGT 880
  A  G  G  A  R  S  G  S  V  K  S  A  I  G  L  G  M  L  L  A  E  G  I  G  D  T
TACGTATCTCACTCGCGGCAGATCCTGTTGAGGAAGTGAAAGTCGGTTTTGATATTCTAAAATCGTTACGGATCCGCTCA 960
  L  R  I  S  L  A  A  D  P  V  E  E  V  K  V  G  F  D  I  L  K  S  L  R  I  R  S
CGTGGCATCAACTTTATTGCTTGCCCAACCTGTTCACGCCAAGAATTTGATGTGATTGGTACGGTAAATGCTTTGGAGCA 1040
  R  G  I  N  F  I  A  C  P  T  C  S  R  Q  E  F  D  V  I  G  T  V  N  A  L  E  Q
GCGCCTCGAAGATATTATCACGCCGATGGATGTCTCTATTATTGGTTGTGTAGTGAATGGCCCGGGTGAAGCCGAGGTTT 1120
  R  L  E  D  I  I  T  P  M  D  V  S  I  I  G  C  V  V  N  G  P  G  E  A  E  V
CTACTTTAGGTGTGGCTGGCGCGAAAACCAAAAGTGGTTTCTATGAAGATGGCGTTCGCAAAAAAGAGCGTTTTGATAAT 1200
  S  T  L  G  V  A  G  A  K  T  K  S  G  F  Y  E  D  G  V  R  K  K  E  R  F  D  N
GACAATATTATTGATCAGCTTGAGGCGAAAATTCGCGCAAAAGCAGCAATGCTTGATGAAATAACCGTATAAAGATAAAC 1280
  D  N  I  I  D  Q  L  E  A  K  I  R  A  K  A  A  M  L  D  E  I  T  V
CAAGTCGAAAATAATTGTCAAACAACTGGCTCATTGAGGGCCAGTTTTGTTTTTATGACTTTTTG 1345
```

Figure 3A

```
 188   CACCGATAAAAAGACGTAAATCCACCCGAATTTATGTAGGTAACGTGCCTATTGGCGATG   247
       || | || ||   | ||| |||| ||    |||||||||| || |'| || || ||||| | |
1629   CAACTATTAAGCGTCGTGAATCGACAAAAATTTATGTGGGAAATGTACCAATTGGTGGGG  1688

248   GTGCTCCCATTGCTGTCCAATCTATGACGAATACGCGCACGACGGATGTTGAAGCCACTG   307
       ||| || |||||| || |||||| ||||| ||||| ||||| || |||||| |||  ||  |
1689   ATGCGCCTATTGCCGTGCAATCAATGACAAATACTCGCACCACTGATGTGGAAGCGACAG  1748

308   TGCGGCAAATCCAATCACTTGAGCGTGTAGGTGTTGATATCGTCCGCGTGTCTGTTCCTA   367
       |     |||||  ||||||  | ||  |||||  ||||  || |||||| || || || | |
1749   TTGCTCAAATTAAATCATTAGAACGTGTTGGTGCAGATATTGTTCGTGTATCTGTTCCAA  1808

368   CGATGGATGCAGCAGAAGCCTTTAAATTAATTAAGCAGCGCGTGAATGTGCCATTGGTTG   327
       | |||||||| || ||||| |||||| |||||| ||  | ||||||| || | || |
1809   CAATGGATGCTGCGGAAGCATTTAAACAAATTAAACAACAAGTGAATGTTCCGCTCGTAG  1868

428   CGGATATTCACTTTGACTACCGTATCGCGATGAAAGTGGCTGAATATGGTGTTGACTGCC   487
       | |||||||| || |||||| |||||||||| | ||||| || ||||||||| || || ||
1869   CAGATATTCATTTCGACTATCGTATCGCGTTAAAAGTCGCAGAATATGGAGTGGATTGTT  1928

488   TACGAATTAACCCAGGTAATATCGGCAGTGAAGAGCGTATTCGCCAAGTCGTTGATAGTG   547
       |||| || || || || || || || || |||||||| ||  | ||    || |||||| |||
1929   TACGTATCAATCCTGGCAACATTGGTCGTGAAGATCGCGTCCGTGCCGTTGTTGATTGTG  1988

548   CTCGTCATCACAACATTCCTATCCGTATAGGGGTCAATGGCGGGTCACTGGAAAAAGATA   607
       | ||   | || |||||  || |||||  || || || || |||  | |||||||||||
1989   CGCGAGACAAAAATATTCCGATTCGTATTGGTGTAAATGCAGGCTCTTTAGAAAAAGATT  2048

608   TCCAAGAAAATACGGTGAGCCAACACCTGAAGCATTGGTTGAATCAGCAATGCGACATG   667
       | ||||||||||| || || ||||| || ||||| ||| | ||||| ||| |||| ||||
2049   TGCAAGAAAAATATGGCGAACCAACGCCAGAAGCCTTGTTAGAATCCGCATTGCGTCATG  2108

668   TTGATATCTTGGACAGGCTGAATTTCGATCAGTTCAAGGTCAGTGTTAAAGCGTCGGATG   727
       | || ||   | ||   | || || |||||||||||| || || || || |||||  || ||||
2109   TAGAAATTCTAGATCGTCTTAACTTCGATCAGTTTAAAGTGAGCGTAAAAGCCTCCGATG  2168

728   TCTTTCTTGCCGTCGGCTCTTATCGTTTATTGGCGCAAAAAATTGATCAACCACTTCACC   787
       | ||  | ||  || |  ||||||||||||||| ||||  ||  |||| | || || | ||
2169   TATTCTTAGCGGTTGAATCTTATCGTTTACTGGCTAAAGCAATTAAACAGCCTTTACATT  2228

788   TCGGTATTACAGAAGCGGGTGGGGCTCGTTCTGGTTCAGTGAAATCAGCAATTGGTCTTG   847
       | || ||||||||| ||||| || ||    |||| |||| ||||| ||| | ||| | | |
2229   TAGGCATTACAGAAGCAGGTGGCGCACGCGCTGGTGCAGTAAAATCTGCAGTGGGTTTAG  2288
```

Figure 3A (Cont'd)

```
 848 GTATGTTGTTGGCTGAAGGTATCGGCGATACGTTACGTATCTCACTCGCGGCAGATCCTG  907
     | ||||| || |||||| || || |||||||||  ||||  ||||  | ||||||||||||
2289 GAATGTTATTAGCTGAGGGCATTGGCGATACACTACGCGTCTCTTTGGCGGCAGATCCTG 2348

908 TTGAGGAAGTGAAAGTCGGTTTTGATATTCTAAAATCGTTACGGATCCGCTCACGTGGCA  967
     | ||||||  | |||||||||||||||||||  | ||||||  ||||||||| || ||| | || |
2349 TAGAGGAAATCAAAGTCGGTTTTGATATTTTGAAATCTTTACGGATTCGTTCAAGAGGAA 2408

968 TCAACTTTATTGCTTGCCCAACCTGTTCACGCCAAGAATTTGATGTGATTGGTACGGTAA 1027
     | |||||||||||||||||||||||||||| |||||||||||||||||| || ||||| ||||
2409 TTAACTTTATTGCTTGCCCAACCTGTTCTCGCCAAGAATTTGATGTAATCGGTACAGTAA 2468

1028 ATGCTTTGGAGCAGCGCCTCGAAGATATTATCACGCCGATGGATGTCTCTATTATTGGTT 1087
     ||||  |  || ||  ||||||  |||||||||| || ||  |||||||| |||||||| ||||
2469 ATGCGCTAGAACAACGCCTTGAAGATATTATTACACCAATGGATGTATCTATTATCGGTT 2528

1088 GTGTAGTGAATGGCCCGGGTGAAGCCGAGGTTTCTACTTTAGGTGTGGCTGGCGCGAAAA 1147
     |||||||||||||| || || || ||   || ||  | | || ||  | |||| || |
2529 GTGTAGTGAATGGTCCTGGCGAGGCACTCGTCTCCGATCTCGGCGTAACGGGCGGTAACA 2588

1148 CCAAAAGTGGTTTCTATGAAGATGGCGTTCGCAAAAAAGAGCGTTTTGATAATGACAATA 1207
     |||||  ||||  |||     || ||  |  |||   ||||||||||||||||||  || |||
2589 AAAAAAGCGGTTATTATCTTGACGGAGAACGCCAAAAAGAGCGTTTTGATAACGAAGATA 2648

1208 TTATTGATCAGCTTGAGGCGAAAATTCGCGCAAAAGCAGCAATGCTTGATGAAATAACC  1266
     |  |  || | || ||  |||||||| || ||||   |||  |  | ||| || || |
2649 TAGTGAACCAATTAGAAGCAAAAATTCGTGCGAAAGTCGCACGACAAGATCCAAAAAAC  2707
```

Figure 3B

| | | |
|---|---|---|
| 175 | ATGCATAATGAATCACCGATAAAAAGACGTAAATCCACCCGAATTTATGTAGGTAACGTG | 234 |
| | ||||||||  |  ||| ||  ||| |  ||||| || || ||||| || || || ||| | |
| 535 | ATGCATAACCAGGCTCCAATTCAACGTAGAAAATCAACACGTATTTACGTTGGGAATGTG | 594 |
| 235 | CCTATTGGCGATGGTGCTCCCATTGCTGTCCAATCTATGACGAATACGCGCACGACGGAT | 294 |
| | || |||||||||||||||||||| || || || || ||||| ||||||||| ||||| || | |
| 595 | CCGATTGGCGATGGTGCTCCCATCGCCGTACAGTCCATGACCAATACGCGTACGACAGAC | 654 |
| 295 | GTTGAAGCCACTGTGCGGCAAATCCAATCACTTGAGCGTGTAGGTGTTGATATCGTCCGC | 354 |
| | || |||||| || ||    |||||| |  | || || || || || | |||||||||||| | |
| 655 | GTCGAAGCAACGGTCAATCAAATCAAGGCGCTGGAACGCGTTGGCGCTGATATCGTCCGT | 714 |
| 355 | GTGTCTGTTCCTACGATGGATGCAGCAGAAGCCTTTAAATTAATTAAGCAGCGCGTGAAT | 414 |
| | || || || || |||||||| || |||||||| || ||| | || || |||| || || | |
| 715 | GTATCCGTACCGACGATGGACGCGGCAGAAGCGTTCAAACTCATCAAACAGCAGGTTAAC | 774 |
| 415 | GTGCCATTGGTTGCGGATATTCACTTTGACTACCGTATCGCGATGAAAGTGGCTGAATAT | 474 |
| | ||||| |||| || || || |||||| ||||| || || ||| ||||||| || ||||| | |
| 775 | GTGCCGCTGGTGGCTGACATCCACTTCGACTATCGCATTGCGCTGAAAGTAGCGGAATAC | 834 |
| 475 | GGTGTTGACTGCCTACGAATTAACCCAGGTAATATCGGCAGTGAAGAGCGTATTCGCCAA | 534 |
| | || || || || || || |||||||| || |||||||| | |||||||||||||||| | |
| 835 | GGCGTCGATTGTCTGCGTATTAACCCTGGCAATATCGGTAATGAAGAGCGTATTCGCATG | 894 |
| 535 | GTCGTTGATAGTGCTCGTCATCACAACATTCCTATCCGTATAGGGGTCAATGGCGGGTCA | 594 |
| | || |||||  |||| ||   || | ||||||||| ||||||||| || || | ||| || | |
| 895 | GTGGTTGACTGTGCGCGCGATAAAAACATTCCGATCCGTATTGGCGTTAACGCCGGATCG | 954 |
| 595 | CTGGAAAAAGATATCCAAGAAAAATACGGTGAGCCAACACCTGAAGCATTGGTTGAATCA | 654 |
| | |||||||||||| | ||||||||| || || || || || ||  | || ||| | ||||| | |
| 955 | CTGGAAAAAGATCTGCAAGAAAAGTATGGCGAACCGACGCCGCAGGCGTTGCTGGAATCT | 1014 |
| 655 | GCAATGCGACATGTTGATATCTTGGACAGGCTGAATTTCGATCAGTTCAAGGTCAGTGTT | 714 |
| | ||  |||||  |||||||||    | || | |||||| |||||||||||||| ||||| || | |
| 1015 | GCCATGCGTCATGTTGATCATCTCGATCGCCTGAACTTCGATCAGTTCAAAGTCAGCGTG | 1074 |
| 715 | AAAGCGTCGGATGTCTTTCTTGCCGTCGGCTCTTATCGTTTATTGGCGCAAAAAATTGAT | 774 |
| | ||||||||| || ||||||  || || || |  |||||||||||| |||| || | || ||| | |
| 1075 | AAAGCGTCTGACGTCTTCCTCGCTGTTGAGTCTTATCGTTTGCTGGCAAAACAGATCGAT | 1134 |
| 775 | CAACCACTTCACCTCGGTATTACAGAAGCGGGTGGGGCTCGTTCTGGTTCAGTGAAATCA | 834 |
| | || ||  | || || || || ||  || || ||||| |||||  || ||  |||| ||||| | |
| 1135 | CAGCCGTTGCATCTGGGGATCACCGAAGCCGGTGGTGCGCGCAGCGGGGCAGTAAAATCC | 1194 |

Figure 3B (Cont'd)

```
 835  GCAATTGGTCTTGGTATGTTGTTGGCTGAAGGTATCGGCGATACGTTACGTATCTCACTC   894
      || ||||||  |||  ||  ||  || ||||||| ||||||||  |||  | ||  | || ||
1195  GCCATTGGTTTAGGTCTGCTGCTGTCTGAAGGCATCGGCGACACGCTGCGCGTATCGCTG  1254

895  GCGGCAGATCCTGTTGAGGAAGTGAAAGTCGGTTTTGATATTCTAAAATCGTTACGGATC   954
      ||||| |||||  || ||  ||  | ||||||||||| |||||| | |||||| | ||  |||
1255  GCGGCCGATCCGGTCGAAGAGATCAAAGTCGGTTTCGATATTTTGAAATCGCTGCGTATC  1314

955  CGCTCACGTGGCATCAACTTTATTGCTTGCCCAACCTGTTCACGCCAAGAATTTGATGTG  1014
      || || ||  || |||||||| |||  ||  |||||  ||||||||||| ||  ||| ||||||||||||
1315  CGTTCGCGAGGGATCAACTTCATCGCCTGCCCGACCTGTTCGCGTCAGGAATTTGATGTT  1374

1015  ATTGGTACGGTAAATGCTTTGGAGCAGCGCCTCGAAGATATTATCACGCCGATGGATGTC  1074
      || ||||||||| || ||    ||||||| ||||| ||||||||| ||||| ||||||||| ||
1375  ATCGGTACGGTTAACGCGCTGGAGCAACGCCTGGAAGATATCATCACTCCGATGGACGTT  1434

1075  TCTATTATTGGTTGTGTAGTGAATGGCCCGGGTGAAGCCGAGGTTTCTACTTTAGGTGTG  1135
      || |||||| || || ||  |||||||||||||  ||||| ||  |||||||||  | || ||
1435  TCGATTATCGGCTGCGTGGTGAATGGCCCAGGTGAGGCGCTGGTTTCTACACTCGGCGTC  1494

1135  GCTGGCGCGAAAACCAAAAGTGGTTTCTATGAAGATGGCGTTCGCAAAAA  1184
      | ||||  ||| |  |||||  || ||||||||||||||||||  |||||| |
1495  ACCGGCGGCAACAAGAAAAGCGGCCTCTATGAAGATGGCGTGCGCAAAGA  1544
```

Figure 3C

```
1242    GCGCCAGCCACACCTAAAGTAGAAACCTCGGCTTCACCCGGGCCATTCACTACACAACCA    1181
        |||||  ||  |   || |  |  ||    |    ||||||||  ||  ||  ||    || ||
129515  GCGCCGGCGATTCCGATATCAGCTTCTCTCGCTTCACCAGGTCCGTTTACAGCGCAGCCG   129574

1182    ATAATAGAGACATCCATCGGCGTGATAATATCTTCGAGGCGCTGCTCCAAAGCATTTACC    1121
        |  || ||   |||   |||||||    |||   |        ||   ||  ||||   |
129575  AGAACAGCAACTTTAATCGGCGCTTTTATCTTAGAAATATACTCTTCCACTTCATTGGCA   129634

1122    GTACCAATCACATCAAATTCTTGGCGTGAACAGGTTGGGCAAGCAATAAAGTTGATGCCA    961
        |  |  ||  | ||||||  ||    ||    ||  || ||||||  |  ||   ||   ||
129635  ATGCTGATTAGATCAATCTCAATACGGCCGCAAGTCGGGCATGAGATGAGCGTGGCAGCA   129694

962     CGTGAGCGGATCCGTAACGATTTTAGAATATCAAAACCGACTTTCACTTCCTCAACAGGA    901
        |||     |   |   || |||||| ||||  ||    | ||||| || || || |||||
129695  TTGGAGGCTAAGCCGAAAGATTTCAGAAGCTCCCTTGCTACTTTTACCTCTTCTACAGGG   129754

902     TCTGCCGCGAGTGAGATACGTAACGTATCGCCGATACCTTCAGCCAACAACATACCAAGA    841
        |||||     ||||| || || |  || |  ||||| ||||    || |     || ||
129755  TCTGCGCTTAGTGAAATGCGCATGGTGTTCCCGATGCCTTTGCTTAAAATGGCGCCGAGT   129814

842     CCAATTGCTGATTTCACTGAACCAGAACGAGCCCCACCCGCTTCTGTAATACCGAGGTGA    781
        ||  |||   || ||||  || |      ||| |  || || || ||||||||||||||
129815  CCTGCTGCGCTCTTTACTGTGCCGGCAAACAGTGTTCCTGACTCGGTGATCCCGAGGTGA   129874

782     AGTGGTTGATCAATTTTTTGCGCCAATAAACGATAAGAGCCGACGGCAAGAAAGACATCC    721
        || ||| |   ||||  ||  || |    |||||    ||| |||  |||||  || ||
129875  AGCGGGTAGTCAAACGCTTTCGCTGCTTTTCATAAGCCTCGATTGCAAGGTTCACGTCA   129934

722     GACGCTTTAACACTGACCTTGAACTGATCGAAATTCAGCCTGTCCAAGATATCAACATGT    661
        || || || |  |||||  | | | || || |||  ||  || | ||  || || || ||
129935  GAGGCCTTCATGCTGACAATAATATCGTGAAAATCAAGATCCTCAAGAATTTTAATGTGA   129994

662     CGCATTGCTGATTCAACCAATGCTTCAGGTGTTGGCTCACCGTATTTTCTTGGATATCT    601
        |  |||   ||| ||||  |  || ||  || || | |||||||||||||| ||  |
129995  TGAAGTGCGCTTTCTACCATTCCATCGGCAGTCGGATAACCGTATTTTCTAAAATCCGT   130054

602     TTTTCCAGTGACCCGCCATTGACCCCTATACGGATAGGAATGTTGTGATGACGAGCACTA    541
        |||||||  |||  |||  || || || || || || | |||||||      ||
130055  TTTTCCAATGAACCGGCGTTTACTCCGATTCTGATCGGAATGCCTTTGTCTTTGGCCGCT   130114

542     TCAACGACTTGGCGAATACGCTCTTCACTGCCGATATTACCTGGGTTAATTCGTAGGCAG    481
        |  ||| ||  ||    ||     | ||||||||| |||| |||| |||||| |
130115  TTAACAACCGCTTCAACTTTTTCGCGCCGGCCGATATTGCCGGGGTTGATTCGGATTTTA   130174
```

Figure 3C (Cont'd)

```
   482 TCAACACCATATTCAGCCACTTTCATCGCGATACGGTAGTCAAAGTCAATATCCGCAACC     421
       ||  | ||   ||||    ||||||  ||| |    || || || || || ||   ||||
130175 TCTGCGCCGCCTTCAATGGCTTTCAACGCAAGTTTATAATCGAAATGTATGTCAACAACG  130234

422 AATGGCACATTCACGCGCTGCTTAATTAATTTAAAGGCTTCTGCTGCATCCATCGTAGGA     361
       |  || |     | |||||  |||||     || ||| | ||| ||              |||
130235 AGAGGAATGGAAATGCGCTTTTTAATATCCGCAATGGCGTTTGCCGCCCGTTCATCCGGA  130294

362 ACAGACACGCGGACGATATCAACACCTACACGCTCAAGTGATTGGATTTGCCGCACAGTG     301
            ||  || ||||||  |     ||   |      |  |    |  ||||  |  || ||
130295 CATGCTACCCGAACGATTTGGCATCCGGCTTCAGCCAAACGGTTAATTTCCGCAACCGTT  130354

302 GCTTCAACATCCGTCGTGCGCGTATTCGTCATAGATTGGACAGCAA     257
       ||||| |||||     ||   || | ||||| |||||    |||
130355 GCTTCTACATCATGTGTTTTTGTTGTTGTCATGCTTTGGATGACAA  130400
```

Figure 4

```
              v10         v20         v30         v40         v50         v60         v70         v80
AarC    MHNESPIKRRKSTRIYVGNVPIGDGAPIAVQSMTNTRTTDVEATVRQIQSLERVGVDIVRVSVPTMDAAEAFKLIKQRVN
        III::II:IIIIIIIIIIIIIIIIIIIIIIIIIIIIIIIIIIIIIII.II::IIIII.IIIIIIIIIIIIIIIIII:VN
GcpE    MHNQAPIQRRKSTRIYVGNVPIGDGAPIAVQSMTNTRTTDVEATVNQIKALERVGADIVRVSVPTMDAAEAFKLIKQQVN
              ^10         ^20         ^30         ^40         ^50         ^60         ^70         ^80

G (aarC1)
              v90        v100        v110        v120       v130 I     v140        v150        v160
        VPLVADIHFDYRIAMKVAEYGVDCLRINPGNIQSEERIRQVVDSARHHNIPIRIGVNGGSLEKDIQEKYGEPTPEALVES
        IIIIIIIIIIIII:IIIIIIIIIIIIIIIIIIIII:IIIII III.II:.IIIIIIIII:IIIIII:IIIIIIII:II:II
        VPLVADIHFDYRIALKVAEYGVDCLRINPGNIGNEERIRMVVDCAROKNIPIRIGVNAGSLEKDLQEKYGEPTPQALLES
              ^90        ^100        ^110        ^120        ^130        ^140        ^150        ^160 v170        v180        v190        v200        v210        v220        v230        v240
        AMRHVDILDRLNFDQFKVSVKASDVFLAVGSYRLLAQKIDQPLHLGITEAGGARSGSVKSAIGLGMLLAEGIGDTLRISL
        IIIIII IIIIIIIIIIIIIIIIIIIII.IIIIII::IIIIIIIIIIIIIIIIII:IIIIIIII:II:IIIIIIII:II
        AMRHVDHLDRLNFDQFKVSVKASDVFLAVESYRLLAKQIDQPLHLGITEAGGARSGAVKSAIGLGLLLSEGIGDTLRVSL
              ^170        ^180        ^190        ^200        ^210        ^220        ^230        ^240 v250        v260        v270        v280        v290        v300        v310        v320
        AADPVEEVKVGFDILKSLRIRSRGINFIACPTCSRQEFDVIGTVNALEQRLEDIITPMDVSIIGCVVNGPGEAEVSTLGV
        IIIIII:IIIIIIIIIIIIIIIIIIIIIIIIIIIIIIIIIIIIIIIIIIIIIIIIIIIIIIIIIIIIIII IIIIII
        AADPVEEIKVGFDILKSLRIRSRGINFIACPTCSRQEFDVIGTVNALEQRLEDIITPMDVSIIGCVVNGPGEALVSTLGV
              ^250        ^260        ^270        ^280        ^290        ^300        ^310        ^320 v330        v340        v350        v360
        AGAKTKSGFYEDGVRKKERFDNDNIIDQLEAKIRAKAAMLDEITV
        :I::.III:IIIIIII :I:II:::IIIIII:IIIII: III
        TGGNKKSGLYEDGVRK-DRLDNNDMIDQLEARIRAKASQLDEARRIQVQQVEK
              ^330        ^340        ^350        ^360
```

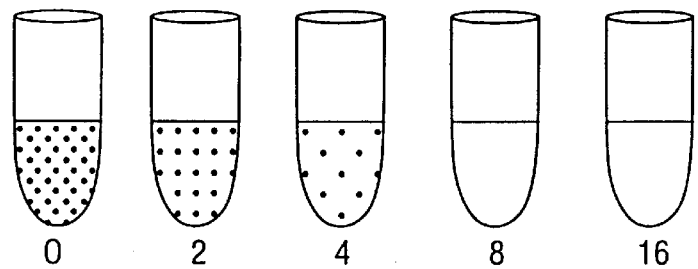
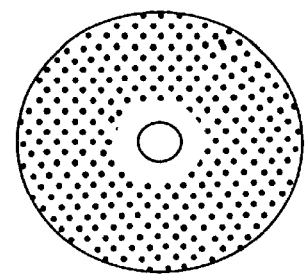
MINIMUM INHIBITORY CONCENTRATION TEST     DISK DIFFUSION TEST
0   2   4   8   16
FIG. 7A
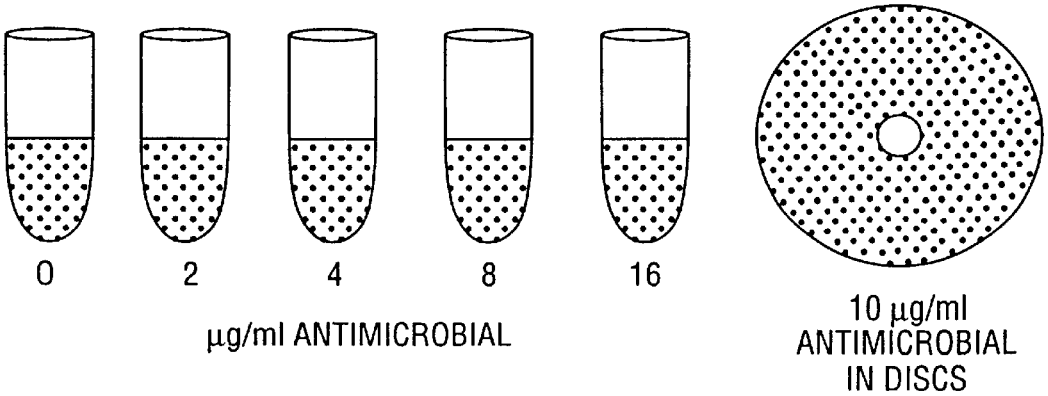
0   2   4   8   16
μg/ml ANTIMICROBIAL     10 μg/ml ANTIMICROBIAL IN DISCS
FIG. 7B

Figure 8

```
                                                         CTCCAGTTAACAAGGTTCATCTGCAA    26
GAAGATTTGGTATTTGTCCATGTTGGAGATAATGATTTTATTATTTTCCCTACACGAGTGTTTTCTTCACAAGAAGAGT   105
TTCAGCAACTTTATTCGTTTATTAAAAAGCAAATCGAGCGACATACGGTGCCATAATAAGCTGTTAAGTGAAGAAAAGT   184
              -35                    -10                       Taq I
GCACGATTGTTTCGCTTTTTGGTGGTTCAATGGCGTTATAATGTATCGGTATCTTTAATCGACTTTAATATAGGTTTTT   263

ATG GGC ATA GAA TAC CGC AGT CTG CAT ACC AGC CAA TTG ACA CTG AGT GAA AAA GAA GCG   323
Met gly ile glu tyr arg ser leu his thr ser gln leu thr leu ser glu lys glu ala CTT TAC GAT TTA TTA ATT GAA GGT TTT GAA GGC GAT TTT TCG CAT GAC GAT TTC GCG CAC   383
leu tyr asp leu leu ile glu gly phe glu gly asp phe ser his asp asp phe ala his
                                                    Bcl I
ACT TTA GGT GGA ATG CAC GTC ATG GCT TTT GAT CAA CAA AAA TTG GTT GGT CAT GTT GCA   443
thr leu gly gly met his val met ala phe asp gln gln lys leu val gly his val ala ATT ATT CAA CGC CAT ATG GCC CTA GAT AAT ACG CCT ATC TCT GTA GGG TAT GTT GAA GCG   503
ile ile gln arg his met ala leu asp asn thr pro ile ser val gly tyr val glu ala ATG GTA GTT GAA CAA AGT TAT CGT CGC CAA GGT ATT GGG CGG CAA TTG ATG CTG CAA ACC   563
met val val glu gln ser tyr arg arg gln gly ile gly arg gln leu met leu gln thr AAT AAA ATT ATA GCT TCG TGT TAT CAA TTA GGG CTG CTG TCG GCT TCA GAT GAT GGA CAA   623
asn lys ile ile ala ser cys tyr gln leu gly leu leu ser ala ser asp asp gly gln AAA TTG TAT CAT TCG GTT GGA TGG CAA ATC TGG AAA GGT AAG TTG TTT GAA TTG AAA CAA   683
lys leu tyr his ser val gly trp gln ile trp lys gly lys leu phe glu leu lys gln GGG AGC TAT ATC CGT TCT ATT GAA GAA GAA GGC GGA GTC ATG GGC TGG AAA GCG GAT GGT   743
gly ser tyr ile arg ser ile glu glu glu gly gly val met gly trp lys ala asp gly
                                                                         Bcl I
GAG GTT GAT TTT ACC CCT TCG CTT TAC TGT GAT TTT CGT GGC GGT GAT CAG TGG TAA TCA   803
glu val asp phe thr ala ser leu tyr cys asp phe arg gly gly asp gln trp OCB AAATTGATAATATAGCGTTATTATTCTGGATTACTGTTAATAATATTTAGGTTAGTTTTCATTTTATTGATAAAAATAA    882
AACCATTAAATGGTAATCCAGTTTGACAACAAAATTGTTATATATAGAATACAGGCTGATTTTTAGTCTAAGGACTCGT    961
AAGCGTTTACGTTAATCAACGCATATAACTTGTCATGCAACAGTTATATGCTGTTGTGTTCGTCTTATTTGGAGTCTGC   1040
ACGATGTCTTCACAAAATAAAAATACCCTCTTTGGAATACCTAAACTTCCCACCAGAGCACTGATCTTTTTGATCCACA   1119
                           Taq I
GGACGGGTGTGGTCGCCATGATCGCGTAGTCGATAGTGGCTCCAAGTAGCGAAGCGAGCAGGACTGGGCGGCGGCCAAA   1198
GCGGTCGGACAGTGCTCCGAGAACGGGTGCGCATAGAAATTGCATCAACGCATATAGCGCTAGCAGCACGCCATAGTGA   1277
CTGCCGATGCTGTCGGAATGGACGATATC                                                    1306
```

METHODS OF SCREENING FOR ANTI-MICROBIAL UTILIZING AARC AND COMPOSITIONS THEREOF

This Application is a divisional of U.S. application Ser. No. 08/827,190, filing date Mar. 27, 1997 now U.S. Pat. No. 5,858,367.

This invention was made with Government support under Grant No.: MCB9405882 awarded by the National Science Foundation. The Government has certain rights in this invention.

FIELD OF THE INVENTION

The present invention relates to nucleic acid sequences of the aarC gene, amino acid sequences of the AarC polypeptide and to methods for screening compositions for their antimicrobial activity and for the detection of organisms susceptible to antimicrobials.

BACKGROUND OF THE INVENTION

Resistance of nosocomial and community-acquired pathogens to antimicrobial agents is a serous problem with significant clinical and economic consequences. Many species are resistant to commonly used antimicrobials, and in many cases resistance to multiple classes of drugs is reported. In the past few years, a handful of organisms resistant to all known antimicrobial agents has emerged [see, Tenover et al., Am. J. Med. Sci. 311:9–16 (1996)]. Though such organisms are rare, the existence of conditions favoring the development and spread of these organisms forecasts the continued emergence of multi-drug resistance. This problem is further exacerbated by the scarcity of new classes of antimicrobial agents since many pharmaceutical manufacturers have abandoned the discovery of antimicrobial drugs in favor of identifying antifungal and antiviral drugs [see, Tenover et al., JAMA 275(4):300–4, 1996].

Antimicrobial drug resistance has been documented in both gram-negative and gram-positive bacterial pathogens. Among the clinically significant gram-negative bacteria, which account for 60% of infections treated in hospitals, resistance to multiple drugs has been reported in *Escherichia coli, Klebsiella pneumoniae, Pseudomonas aeruginosa, Haemophilus influenzae*, and *Neisseriae gonorrhoeae*. Multiple-drug resistance is also found in gram-positive bacteria, such as *Staphylococcus aureus, Staphylococcus hemolyticus*, and *Streptococcus pneumoniae* which are isolated from hospital environments. Because resistance to multiple classes of drugs is rapidly spreading among clinically significant bacterial isolates, the clinical and economic consequences of multiple-drug resistance are severe.

A. Antimicrobial Drug Resistance

Three key factors have contributed to the emergence and spread of microbes which are resistant to multiple antimicrobial compounds, including mutations in common resistance genes, exchange of genetic information among microorganisms, and the increased selective pressures in institutional settings and communities.

Mutations in common resistance genes have extended the bacterial spectrum of drug resistance. Resistance genes mostly encode proteins that either inactivate antimicrobial agents or block their site of action. For example, the organism may alter the receptors to which the antimicrobial binds (e.g., conformational changes in penicillin binding proteins (PBPs), such that penicillin won't bind), or it alter the cell membrane such that membrane transport systems are ineffective in transporting the antimicrobial across the cell membrane (e.g., resistance to tetracyclines due to the fact that the drug cannot enter the cell). Alternatively, the organism can develop enzymes which destroy or inactivate the antimicrobial (e.g., β-lactamases which destroy penicillin). In addition, the organism can also alter an enzyme's specificity for its substrate (e.g., sulfonamide-resistant bacteria often have enzymes with a high affinity for para-aminobenzoic acid (PABA), but a low affinity for sulfonamide), or altogether forego its requirement for a particular substrate (e.g., exogenous folic acid may be taken in by sulfonamide-resistant bacteria, thereby by-passing the need to take in PABA as a precursor of folic acid synthesis). Importantly, microorganisms that are resistant to a given drug may also be resistant to other drugs that share certain mechanisms of action. This cross-resistance is usually observed with drugs that are closely related chemically or that have a similar mode of binding or action.

Small changes in resistance determinants (e.g., enzymes) can also have major effects on an organism's resistance profile to drugs which belong to different chemical classes. This is exemplified by the changes in β-lactamases. These enzymes inactivate β-lactam drugs such as penicillin, ampicillin, and cephalothin. Mutant forms of the β-lactamases, which are referred to as extended-spectrum β-lactamases (ESBLs) and which are capable of inactivating the chemically unrelated extended-spectrum cephalosporins and monobactams were reported as early as 1982. Only three amino acid differences, which reflect point mutations in the coding sequence of the β-lactamase, exist between the ESBL and wild-type β-lactamases.

The problem of multiple-resistant bacteria is compounded by the exchange of genetic information between bacteria. Bacteria exchange information by transformation (i.e., the uptake of naked DNA), transduction (i.e., transfer of DNA by bacteriophage), and conjugation (i.e., cell-to-cell contact). The exchange of extrachromosomal elements such as plasmids and transposons during conjugation is the most common method of resistance transfer. Although conjugation was previously thought to be limited to gram-negative bacilli, a similar transfer process has been extensively documented for gram-positive organisms whereby plasmids or independent transposable elements, often carrying multiple-resistance genes, move from one organism to another. The transfer process extends even between gram-negative and gram-positive organisms. For example, *Campylobacter coli* and enterococci have been shown to exchange aminoglycoside resistance genes {Trieu-Cuot et al., EMBO J. 4:3583–3587 (1985)]. Thus, a susceptible strain can acquire resistance from another resistant species or genus.

Environmental pressures encourage the emergence or acquisition of new mutations. Such pressures include the extended and prophylactic use of antimicrobials in communities, hospitals, nursing homes, day care centers and animal feedlots. In addition, many antimicrobials are bacteriostatic rather than bacteriocidal. Organisms exposed to bacteriostatic drugs remain viable, although their growth is inhibited. Because they remain viable, these organisms are provided with the opportunity to develop mechanisms of resistance to the drug. For example, the use in hospitals of antimicrobials prone to select altered resistance traits results in hospitalized patients, who are usually immunocompromised, quickly becoming colonized with resistant strains.

B. Addressing Antimicrobial Drug Resistance

Attempts to minimize the impact of multiple-drug resistance have focused on barrier isolation, improvement of antimicrobial use, and proper design and use of instruments.

Barrier isolation precautions aim to contain infection by reducing a hospitalized patient's physical contact with bacteria. Although such precautions are effective against bacteria from exogenous sources, they are of limited use in containing organisms endogenous to the patient. Furthermore, regardless of the quality of isolation precautions, they are ineffective in containing antimicrobial drug resistance which arises by mutation, genetic transfer, emergence, and selection of resistant strains. In addition, though manageable in a hospital setting, isolation precautions are often impractical in the community.

Avoiding the misuse of antimicrobials is also important in dealing with multiresistant organisms. While controlling the use of antimicrobials in hospitals may go a long way towards minimizing the problem, such control is difficult to enforce. Moreover, the benefits of controlled antimicrobial use in hospitals are often thwarted by the slower conformance in the community to judicious antimicrobial drug use.

An additional attack on problems of multiresistance includes proper design and use of instruments. Some organisms have attributes, independent of their ability to resist antimicrobials, which allow them to survive in or around instruments, thus making instruments a vehicle for dissemination of resistance and a reservoir of hospital organisms. Though better instrument design and use may reduce the dissemination of such organisms, it nevertheless does not address the development of antimicrobial drug resistance via mutation and selection.

What is needed is a new gene or gene product which can be targeted by classes of antimicrobials that are different from those currently used and to which microbial resistance is established. Discovery of such new genes and their products is particularly useful where they are present in more than one microbial strain, and found in both gram-negative and gram-positive microbes.

SUMMARY OF THE INVENTION

In one embodiment, the present invention provides a substantially purified polypeptide comprising at least a portion of the amino acid sequence of SEQ ID NO:5. In one preferred embodiment, the purified polypeptide comprises a portion of the SEQ ID NO:5 having a length greater than about 65 amino acid residues, more preferably greater than about 75 amino acid residues, and most preferably greater than about 90 amino acid residues.

In another embodiment, the invention provides an isolated polynucleotide sequence encoding a polypeptide comprising at least a portion of the amino acid sequence of SEQ ID NO:5. In one embodiment, the polynucleotide sequence is contained on a recombinant expression vector. In a further preferred embodiment, the expression vector containing the polynucleotide sequence is contained within a host cell.

In yet another embodiment, the invention provides a polynucleotide sequence that hybridizes under stringent conditions to the nucleic acid sequence of SEQ ID NO:4.

In a further embodiment, the invention provides a method of screening a compound, the method comprising: a) providing, in any order: i) bacteria containing a recombinant expression vector, wherein the vector comprises at least a portion of the oligonucleotide sequence of SEQ ID NO:4 or variants or homologs thereof; and ii) a compound suspected of having antimicrobial activity; b) contacting the bacteria with the compound; and c) detecting antimicrobial activity of the compound. In one preferred embodiment, the antimicrobial activity is bacteriostatic. In a further preferred embodiment, the antimicrobial activity is bactericidal. In yet a further preferred embodiment, the bacteria are gram negative. In a further preferred embodiment, the gram negative bacteria is *Escherichia coli*. In an alternative preferred embodiment, the bacteria are gram positive. In a further preferred embodiment, the gram positive bacteria is *Bacillus subtilis*.

In one embodiment of the method of screening a compound, the vector further comprises a fusion sequence, wherein the fusion sequence comprises a reporter sequence operably linked to aac(2')-la. In a particularly preferred embodiment, the reporter sequence is a β-galactosidase sequence.

Yet another embodiment of the invention provides a method for detecting the presence of polynucleotide sequences encoding at least a portion of aarC gene in a sample, the method comprising the steps of: a) providing in any order: i) at least a portion of the nucleotide of SEQ ID NO:4, or a variant or homolog thereof; and ii) a sample suspected of containing nucleic acid corresponding to at least a portion of the polynucleotide sequence of SEQ ID NO:4 or variants or homologs thereof, b) combining the nucleotide and the sample under conditions such that a hybridization complex is formed between the nucleotide sequence and the polynucleotide; and c) detecting the hybridization complex. In one preferred embodiment, the nucleotide sequence is RNA. In another preferred embodiment, the nucleotide sequence is DNA. In one embodiment, the detected hybridization complex correlates with expression of the at least portion of the polynucleotide of SEQ ID NO:4 or variants of homologs thereof in the sample.

In another embodiment, the invention provides a purified antibody which binds specifically to a polypeptide comprising at least a portion of the amino acid sequence of SEQ ID NO:5.

In yet another embodiment, the invention provides a method for detecting the expression of AarC in a sample, the method comprising the steps of: a) providing in any order: i) an antibody which binds specifically to a polypeptide comprising at least a portion of the amino acid sequence of SEQ ID NO:5; and ii) a sample suspected of expressing AarC; b) combining the sample and the antibody under conditions such that an antibody:protein complex is formed; and c) detecting the complex wherein the presence of the complex correlates with the expression of the protein in the sample. In one preferred embodiment, the antibody is polyclonal. In another preferred embodiment, the antibody is monoclonal.

DEFINITIONS

To facilitate understanding of the invention, a number of terms are defined below.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

"Amino acid sequence" and "polypeptide sequence" are used interchangeably herein to refer to a sequence of amino acids.

As used herein, "AarC" or "AarC polypeptide" or "AarC protein" are used interchangeably to refer to the amino acid sequence of substantially purified AarC obtained from any species, particularly bacterial species which include gram negative, gram positive, aerobic, and anaerobic bacteria, and obtained from any source whether natural, synthetic, semi-synthetic or recombinant.

A "variant" of AarC is defined as an amino acid sequence which differs by one or more amino acids from the AarC polypeptide sequence of SEQ ID NO:5. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software.

A "variant" of aarC is defined as a nucleotide sequence which differs from SEQ ID NO:4, e.g., by having deletions, insertions, and substitutions that may be detected using hybridization assays. Included within this definition is the detection of alterations to the genomic DNA sequence which encodes AarC [e.g., by alterations in the pattern of restriction enzyme fragments capable of hybridizing to SEQ ID NO:4 (RFLP analysis), the inability of a selected fragment of SEQ ID NO:4 to hybridize under high stringency conditions to a sample of genomic DNA (e.g., using allele-specific oligonucleotide probes), and improper or unexpected hybridization, such as hybridization to a locus other than the normal chromosomal locus for the aarC gene (e.g., using fluorescent in situ hybridization (FISH)).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring *Providencia stuartii* AarC.

A "substitution" results from the replacement of one or more nucleotides or amino acids by different nucleotides or amino acids, respectively.

The term "derivative" of aarC as used herein refers to the chemical modification of a nucleic acid encoding AarC. Illustrative of such modifications would be replacement of hydrogen by an alkyl, acyl, or amino group. A nucleic acid derivative would encode a polypeptide which retains essential biological characteristics of natural human AarC.

As used herein the term "portion" when in reference to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:5" encompasses the full-length human AarC protein and fragments thereof.

The term "portion" when used in reference to a nucleotide sequence refers to fragments of that nucleotide sequence. The fragments may range in size from 5 nucleotide residues to the entire nucleotide sequence minus one nucleic acid residue.

The term "biologically active" refers to a AarC molecule having structural, regulatory or biochemical functions of a naturally occurring AarC. AarC biological activity is determined, for example, by restoration of wild-type growth in cells lacking AarC activity (i.e., AarC null cells). Cells lacking AarC activity may be produced using methods well known in the art (e.g., point mutation and frame-shift mutation). Complementation is achieved by transfecting cells which lack AarC activity with an expression vector which expresses AarC, a derivative thereof, or a portion thereof. Details concerning complementation of AarC null cells is provided in Example 3 herein.

The term "immunologically active" defines the capability of the natural, recombinant or synthetic AarC, or any oligopeptide thereof, to induce a specific immune response in appropriate animals or cells and to bind with specific antibodies.

The term "antigenic determinant" as used herein refers to that portion of a molecule that is recognized by a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "immunogen," "antigen," "immunogenic" and "antigenic" refer to any substance capable of generating antibodies when introduced into an animal. By definition, an immunogen must contain at least one epitope (the specific biochemical unit capable of causing an immune response), and generally contains many more. Proteins are most frequently used as immunogens, but lipid and nucleic acid moieties complexed with proteins may also act as immunogens. The latter complexes are often useful when smaller molecules with few epitopes do not stimulate a satisfactory immune response by themselves.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabelled A) in a reaction containing labelled "A" and the antibody will reduce the amount of labelled A bound to the antibody.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

An oligonucleotide sequence which is a "homolog" of the P. Stuartii aarC gene of SEQ ID NO:4 is defined herein as an oligonucleotide sequence which exhibits greater than or equal to 50% identity to the sequence of SEQ ID NO:4 when sequences having a length of 100 bp or larger are compared. Alternatively, a homolog of SEQ ID NO:4 is defined as an oligonucleotide sequence which encodes a biologically active AarC amino acid sequence.

Low stringency conditions comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (ie., it is the complement of) the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_0t$ or $R_0t$ analysis) or between one nucleic acid sequence present in solution and another nucleic acid sequence immobilized to a solid support [e.g., a nylon membrane or a nitrocellulose filter as employed in Southern and Northern blotting, dot blotting or a glass slide as employed in in situ hybridization, including FISH (fluorescent in situ hybridization)].

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl [see e.g., Anderson and Young, Quantitative Filter Hybridization, in *Nucleic Acid Hybridization* (1985)]. Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. As will be understood by those of skill in the art, a stringent hybridization can be used to identify or detect identical polynucleotide sequences or to identify or detect similar or related polynucleotide sequences. The stringent conditions are chosen such that SEQ ID NO:4 or fragments thereof will hybridize to sequences encoding AarC but not to sequences encoding GpcE (i.e., SEQ ID NO:6) or RNA equivalents of GpcE. When fragments of SEQ ID NO:4 are employed in hybridization reactions, the stringent conditions include the choice of fragments of SEQ ID NO:4 to be used. Fragments of SEQ ID NO:4 which contain unique sequences (i.e., regions which are either non-homologous to or which contain less than about 50% homology or complementarity with SEQ ID NOs:4) are preferentially employed. SEQ ID NO: 4 represents a DNA sequence encoding the AarC protein; this DNA sequence can be found in GenBank under accession number U67933. Fragments of SEQ ID NO:4 which contain unique sequences (i.e., regions which are either non-homologous to or which contain less than 50% homology or complementarity with SEQ ID NO:4) are preferentially employed. Conditions of "weak" or "low" stringency are often required with nucleic acids that are derived from organisms that are genetically diverse, as the frequency of complementary sequences is usually low between such organisms.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interst. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction technologies well known in the art [Dieffenbach CW and GS Dveksler (1995) *PCR Primer, a Laboratory Manual*, Cold Spring Harbor Press, Plainview N.Y.]. As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage.

Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription [Maniatis, T. et al., *Science* 236:1237 (1987)]. Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site [Sambrook, J. et al., *Molecular Cloning: A Laboratory Manual*, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "transfection" or "transfected" refers to the introduction of foreign DNA into a cell.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "antisense" is used in reference to RNA sequences which are complementary to a specific RNA sequence (e.g., MRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists [J. Sambrook et al. (1989) *Molecular Cloning: A Laboratory Manual*, Cold Spring Harbor Press, N.Y., pp 9.31–9.58].

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists [J. Sambrook, J. et al. (1989) supra, pp 7.39–7.52].

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonuclotide probe or RNA probe to detect DNA species complementary to the ribo probe used.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a AarC polypeptide includes, by way of example, such nucleic acid in cells ordinarily expressing a AarC polypeptide where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (ie., the oligonucleotide may be double-stranded).

As used herein, the term "purified" or "to purify" refers to the removal of undesired components from a sample. For example, where recombinant AarC polypeptides are expressed in bacterial host cells, the AarC polypeptides are purified by the removal of host cell proteins thereby increasing the percent of recombinant AarC polypeptides in the sample.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g. milk), and solid foods (e.g., vegetables). A biological sample suspected of containing nucleic acid encoding AarC may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), CDNA (in solution or bound to a solid support) and the like.

The term "antimicrobial" and "antibacterial" are used interchangeably to refer to a composition which reduces the rate of growth of an organism compared to the rate of growth of the organism in the absence of the composition. An antimicrobial can be natural (e.g., derived from bacteria), synthetic, or recombinant. An antimicrobial can be bacteriostatic, bactericidal or both. An antimicrobial is bacteriostatic if it inhibits cell division without affecting the viability of the inhibited cell. An antimicrobial is bactericidal if it causes cell death. Cell death is commonly detected by the absence of cell growth in liquid growth medium (e.g., absence of turbidity) or on a solid surface (e.g., absence of colony formation on agar). Those of skill in the art know that a composition which is bacteriostatic at a given concentration may be bactericidal at a higher concentration. Certain bacteriostatic compositions are not bactericidal at any concentration.

The term "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. Also included within this term are prokaryotic organisms which are gram negative or gram positive.

"Gram negative" and "gram positive" refer to staining patterns with the Gram-staining process which is well known in the art [Finegold and Martin, Diagnostic Microbiology, 6th Ed. (1982), C V Mosby St. Louis, pp 13–15]. "Gram positive bacteria" are bacteria which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

BRIEF DESCRIPTION OF THE INVENTION

The present invention is premised on the fortuitous discovery of the aarC gene in *Providencia stuartii*. Data presented herein demonstrates that the wild-type form of the aarC gene shown in FIG. 2 (SEQ ID NO:4) is essential to the viability of *Providencia stuartii*. A transversion in the nucleic acid sequence of this gene leading to a single amino acid substitution resulted in a very slow growing phenotype. In addition, disruption of the aarC gene by insertion of a nucleic acid sequence within the aarC gene resulted in cell death.

*Providencia stuartii* is a member of the family Enterobacteriaceae. It is a nosocomial pathogen which exhibits multiple resistance to antibiotics and is responsible for a variety of human infections, particularly nosocomial urinary tract infections which are more prevalent in older patients. *P. stuartii* has also been reported in hospital patients with bacteraemia, septicaemia associated with burns, and in non-specific diarrhea in infants under one year of age. Despite the apparently low virulence of the organism, it can cause extensive and long-term outbreaks of infection with fatalities in specialized hospital units such as intensive therapy units and burns units [Hawkey, P. Journal of Antimicrob. Chemotherapy 13:209–226 (1984)].

*P. stuartii* is resistant to several classes of antimicrobials, including the aminoglycoside and cephalosporin antibiotics [Penner et al. Antimicrobial Agents and Chemotherapy 22:218–221 (1982)] and substituted penicillin [Hawkey et al., Antimicrobial Agents and Chemotherapy 23:619–621 (1983)]. For example, many of the first- and second-generation cephalosporins are susceptible to the β-lactamases produced by *P. stuartii*, with 97% resistance rates being reported to cephalothin, 82% to cephaloridine, 94% to cefazolin, and 100% to cephalexin [Hawkey, P. Journal of Antimicrob. Chemotherapy 13:209–226 (1984)]. In addition, and in common with other gram-negative bacteria, *P. stuartii* is resistant to aminoglycoside antibiotics. High proportions of *P. stuartii* (80–100%) were resistant to gentamicin both in wards where the drug is widely used and in others (e.g., geriatric wards) in which it was not used at all.

The resistance of *P. stuartii* to aminoglycoside antimicrobials results partly from the production of the chromosomally encoded aminoglycoside-inactivating enzyme aminoglycoside N-acetyltransferase (2'), i.e., AAC(2')-la, which is encoded by the aac(2')-la gene (SEQ ID NO:12) (FIG. 8) previously described by Rather et al. (1993) J. Bacteriol. 175:6492–6498. This enzyme was initially identified by its role in aminoglycoside resistance [Chevereau, M. et al., Biochemistry 13:598–603 (1974), Rather, P. et al., J. Bacteriol. 175:6492–6498 (1993), Yamaguchi, M. et al., J. Antibiotics 27:507–515 (1974)]. AAC(2')-la is presumed to acetylate aminoglycosides because of their structural similarity with the peptidoglycan substrates of this enzyme. This enzyme is believed to have, in addition to its known role in aminoglycoside resistance, an important housekeeping function in the O-acetylation of peptidoglycan.

The aac(2')-la gene is universally present in the chromosome of *P. stuartii* regardless of resistance phenotype. Regulation of aac(2')-la expression is complex. Recessive mutations in at least four loci (i.e., aarA, aarB, aarD, and aarG) have been identified that increase aac(2')-la mRNA accumulation [Macinga et al. (1981) Mol. Microbiol. 19:511–520; Rather et al. (1993) J. Bacteriol. 175:6492–6498]. In addition, a gene (aarP) encoding a transcriptional activator (AarP) has also been identified [Macinga, D. R. et al. J. Bacteriol. 177:3407–3413 (1995)]. An additional level of regulation of the aac(2')-la gene includes repression mediated by a diffusible extracellular factor, AR-factor, which acts by an unknown mechanism to decrease aac(2')-la mRNA accumulation as cells approach high density.

The present invention provides nucleic acid sequences encoding *P. stuartii* AarC and its variants. The aarC gene was discovered in the course of an investigation of negative regulators of the aac(2')-la gene. The present invention provides results which demonstrate that the wild-type aarC gene is essential for cell viability. A missense allele (aarC1) resulted in an 8.9-fold increase in β-galactosidase accumulation from an aac(2')-lacZ transcriptional fusion. Northern blot analysis demonstrated that this increase was specific to aac(2')-lacZ mRNA accumulation. mRNA encoding AarP (a transcription activator of the aac(2')-la gene) was also elevated in *P. stuartii* cells containing the aarC1 allele. Both the elevation of aac(2')-lacZ mRNA and aarP mRNA were observed only in cells at high density. While not intending to limit the invention to any particular mechanism, the observation that aarC-mediated regulation of aac(2')-la and of aarP is specific to cells at high cell density suggests that aarC may act in a pathway by which *P. stuartii* responds to extracellular factor(s) involved in regulating aac(2')-la expression.

The wild-type aarC gene (SEQ ID NO:4) of the present invention was isolated by complementation and was shown to encode a predicted AarC polypeptide sequence (SEQ ID NO:5) of 366 amino acids with a molecular weight of 39815 Da. The predicted AarC polypeptide sequence was homologous to amino acid sequences from gram negative and gram positive bacteria. Thus, the AarC polypeptide exhibited 88% amino acid homology to the previously identified GcpE protein of *Escherichia coli*, a gene product whose function is unknown and reported to be essential [Baker, J. et al., FEMS Microbiolgy Letters 92:175–180 (1992), Eisenbeis, S. J. et al., Mol. Gen. Genet. 183:115–122 (1981)], and 86% homology to a gene product from *Haemophilus influenzae*. AarC also showed 51% homology to a *B. subtilis* protein.

As demonstrated herein, the *E. coli* gcpE gene was able to functionally complement the aarC1 allele in *P. stuartii*. The aarC1 allele was identified as a T to G transversion that resulted in a valine to glycine substitution at position 136 in the AarC polypeptide. The present invention demonstrates that the aarC gene is essential for cell viability as construction of a disrupted copy (aarC::lacZ) of the gene was possible only in cells that carried an episomal copy of aarC or gcpE. The essential nature of aarC in *P. stuartii* and the conservation of this gene product in three different gram negative organisms as well as in a gram positive organism make the aarC gene and its product, the AarC polypeptide, attractive targets for the development of new antimicrobials.

I. The aarC Nucleotide Sequence

The nucleic acid sequence of the aarC gene (SEQ ID NO:4) and the amino acid sequence of the AarC polypeptide (SEQ ID NO:5) encoded by this gene are shown in FIG. 2. While the precise function of the AarC polypeptide is unclear, data presented in this invention demonstrates that it performs a function which is essential to the microbe's survival. This conclusion is based in part on (a) the homology of the AarC polypeptide to proteins from the gram negative *E. coli* and *H. influenzae* and the gram positive *B. subtilis*, (b) the very slow growing cell phenotype which resulted from a single point mutation in the aarC sequence, (c) cell death as a result of disruption of the aarC gene, and (d) generation of viable cells by complementation of a disrupted aarC gene with an episomal copy of the wild-type aarC gene.

The present invention contemplates any nucleic acid sequence which encodes the AarC polypeptide sequence or its variants; these nucleic acid sequences are used to make recombinant molecules which express the AarC polypeptide. For example, one of ordinary skill in the art would recognize that the redundancy of the genetic code permits an enormous number of nucleic acid sequences which encode the AarC polypeptide. Thus, codons which are different from those shown in FIG. 2 may be used to increase the rate of expression of the nucleotide sequence in a particular prokaryotic or eukaryotic expression host which has a preference for particular codons. Additionally, alternative codons may also be used in eukaryotic expression hosts to generate splice variants of recombinant RNA transcripts which have more desirable properties (e.g., longer or shorter half-life) than transcripts generated using the sequence depicted in FIG. 2. In addition, different codons may also be desirable for the purpose of altering restriction enzyme sites or, in eukaryotic expression hosts, of altering glycosylation patterns in translated polypeptides.

Variants of the nucleotide sequence of FIG. 2 are also included within the scope of this invention. These variants include, but are not limited to, nucleotide sequences having deletions, insertions or substitutions of different nucleotides or nucleotide analogs as long as the biological activity of the translation product of the nucleotide sequence is maintained.

This invention is not limited to the aarC sequence (SEQ ID NO:4) but specifically includes nucleic acid homologs which are capable of hybridizing to the nucleotide sequence of FIG. 2, and to portions, variants and derivatives thereof. Those skilled in the art know that different hybridization stringencies may be desirable. For example, whereas higher stringencies may be preferred to reduce or eliminate non-specific binding between the nucleotide sequence of FIG. 2 and other nucleic acid sequences, lower stringencies may be preferred to detect a larger number of nucleic acid sequences having different homologies to the nucleotide sequence of FIG. 2.

Fragments of the aarC sequence (SEQ ID NO:4) are also specifically contemplated to be within the scope of this invention. It is preferred that the fragments have a length equal to or greater than 10 nucleotides and show greater than 50% homology to SEQ ID NO:5. These fragments are exemplified by, but not restricted to, the sequence 5'-CACTGTGCGG-3' (SEQ ID NO:11) which is located between the nucleotide 303–312 of SEQ ID NO:2.

The present invention further contemplates antisense molecules comprising the nucleic acid sequence complementary to at least a portion of the polynucleotide of SEQ ID NO:4.

The scope of this invention further encompasses nucleotide sequences containing the nucleotide sequence of FIG. 2, portions, variants, derivatives and homologs thereof, ligated to one or more heterologous sequences as part of a fusion gene. Such fusion genes may be desirable, for example, to detect expression of sequences which form part of the fusion gene. Examples of a heterologous sequence include the reporter sequence encoding the enzyme β-galactosidase or the enzyme luciferase. Fusion genes may also be desirable to facilitate purification of the expressed protein. For example, the heterologous sequence of protein A allows purification of the fusion protein on immobilized immunoglobulin. Other affinity traps are well known in the art and can be utilized to advantage in purifying the expressed fusion protein. For example, pGEX vectors (Promega, Madison Wis.) may be used to express the AarC polypeptides as a fusion protein with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

The nucleotide sequence shown in FIG. 2, portions, variants, derivatives and homologs thereof can be synthesized by synthetic chemistry techniques which are commercially available and well known in the art. The nucleotide sequence of synthesized sequences may be confirmed using commercially available kits as well as from methods well known in the art which utilize enzymes such as the Klenow fragment of DNA polymerase I, Sequenase®, Taq DNA polymerase, or thermostable T7 polymerase. Capillary electrophoresis may also be used to analyze the size and confirm the nucleotide sequence of the products of nucleic acid synthesis. Synthesized sequences may also be amplified using the polymerase chain reaction (PCR) as described by Mullis [U.S. Pat. No. 4,683,195] and Mullis et al. [U.S. Pat. No. 4,683,202], the ligase chain reaction [LCR; sometimes referred to as "Ligase Amplification Reaction" (LAR)] described by Barany, Proc. Natl. Acad. Sci., 88:189 (1991); Barany, PCR Methods and Applic., 1:5 (1991); and Wu and Wallace, Genomics 4:560 (1989).

It is readily appreciated by those in the art that the aarC nucleotide sequences of the present invention may be used in a variety of ways. For example, fragments of the sequence of at least about 10 bp, more usually at least about 15 bp, and up to and including the entire (i.e., full-length) sequence can be used as probes for the detection and isolation of complementary genomic DNA sequences from *P. stuartii* as well as other bacteria. Genomic sequences are isolated by screening a genomic library containing bacterial DNA with all or a portion of the aarC sequence (SEQ ID NO:4). In addition to screening genomic libraries, the aarC sequence can also be used to screen cDNA libraries made using bacterial RNA.

The aarC sequence is also useful in directing the synthesis of AarC. The AarC polypeptide finds use in producing AarC antibodies for diagnostic purposes such as detecting infections with bacteria which express AarC. The aarC sequence is also useful for the screening of antimicrobials and the detection of microbes which contain aarC sequences and their homologs. These uses are described in the following sections.

II. The AarC Polypeptide Sequence

The present invention provides the polypeptide sequence (SEQ ID NO:5) of AarC as shown in FIG. 2 and specifically contemplates variants thereof. For example, AarC variants included within the scope of this invention include AarC polypeptide sequences containing deletions, insertion or substitutions of amino acid residues which result in a polypeptide that is functionally equivalent to the AarC polypeptide of FIG. 2. For example, amino acids may be substituted for other amino acids having similar characteristics of polarity, charge, solubility, hydrophobicity, hydrophilicity and/or amphipathic nature. Alternatively, substitution of amino acids with other amino acids having one or more different characteristic may be desirable for the purpose of producing a polypeptide which is secreted from the cell in order to, for example, simplify purification of the polypeptide.

The AarC polypeptide sequence of FIG. 2 and its functional variants may be made using chemical synthesis. For example, peptide synthesis of the AarC polypeptide, in whole or in part, can be performed using solid-phase techniques well known in the art. Synthesized polypeptides can be substantially purified by high performance liquid chromatography (HPLC) techniques, and the composition of the purified polypeptide confirmed by amino acid sequencing. One of skill in the art would recognize that variants of the AarC polypeptide can be produced by manipulating the polypeptide sequence during and/or after its synthesis.

AarC and its functional variants can also be produced by an expression system. Expression of AarC may be accomplished by inserting the nucleotide sequence of FIG. 2, its variants, portions, derivatives or homologs into appropriate vectors to create expression vectors, and transfecting the expression vectors into host cells.

Expression vectors can be constructed using techniques well known in the art [Sambrook et al. (1989) *Molecular Cloning, A Laboratory Manual*, Cold Spring Harbor Press, Plainview N.Y.; Ausubel et al. (1989) *Current Protocols in Molecular Biology*, John Wiley & Sons, New York N.Y.]. Briefly, the nucleic acid sequence of interest is placed in operable combination with transcription and translation regulatory sequences. Regulatory sequences include initiation signals such as start (i.e., ATG) and stop codons, promoters which may be constitutive (i.e., continuously active) or inducible, as well as enhancers to increase the efficiency of expression, and transcription termination signals. Transcription termination signals must be provided downstream from the structural gene if the termination signals of the structural gene are not included in the expression vector. Expression vectors may become integrated into the genome of the host cell into which they are introduced, or are present as unintegrated vectors. Typically, unintegrated vectors are transiently expressed and regulated for several hours (eg., 72 hours) after transfection.

The choice of promoter is governed by the type of host cell to be transfected with the expression vector. Host cells include bacterial, yeast, plant, insect, and mammalian cells. Transfected cells may be identified by any of a number of marker genes. These include antibiotic (e.g., gentamicin, penicillin, and kanamycin) resistance genes as well as marker or reporter genes (e.g., β-galactosidase and luciferase) which catalyze the synthesis of a visible reaction product.

Expression of the gene of interest by transfected cells may be detected either indirectly using reporter genes, or directly by detecting mRNA or protein encoded by the gene of interest. Indirect detection of expression may be achieved by placing a reporter gene in tandem with the sequence encoding AarC under the control of a single promoter. Expression of the reporter gene indicates expression of the tandem AarC sequence. It is preferred that the reporter gene have a visible reaction product. For example, cells expressing the reporter gene β-galactosidase produce a blue color when grown in the presence of X-Gal, whereas cells grown in medium containing luciferin will fluoresce when expressing the reporter gene luciferase.

Direct detection of AarC expression can be achieved using methods well known to those skilled in the art. For example, mRNA isolated from transfected cells can be hybridized to labelled oligonucleotide probes and the hybridization detected. Alternatively, polyclonal or monoclonal antibodies specific for AarC can be used to detect expression of the AarC polypeptide using enzyme-linked immunosorbent assay (ELISA), radioimmunoassay (RIA) and fluorescent activated cell sorting (FACS).

Recombinant AarC and its variants which are expressed by the host cell can be purified either from the culture medium, if the expression construct directs its secretion into culture medium, or from the host cell using purification techniques known in the art. For example, AarC polypeptide may be expressed as a fusion protein with heterologous metal chelating peptides (ie., polyhistidine tracts) or with protein A domains, and purified on commercially available immobilized metals or immunoglobulins, respectively.

Those skilled in the art recognize that the AarC polypeptide sequences of the present invention are useful in generating antibodies which find use in detecting bacteria that express AarC or proteins homologous thereto. Such detection is particularly useful in the choice of antimicrobials to be used in a clinical context. For example, a clinical sample (e.g., a urethral or genital exudate, blood, wound culture, or respiratory culture) which shows the presence of proteins reactive with AarC antibodies indicates the presence of bacteria which contain aarC. This further suggests that it may be advantageous to administer antimicrobials which alter AarC activity to the patient from whom the sample was derived.

III. Methods For Screening Compounds For Antimicrobial Activity

This invention contemplates methods for screening compounds for antimicrobial activity which alter the activity of AarC. As used herein, the term "antimicrobial" is intended to mean a compound which is bacteriostatic, bactericidal or both. Such compounds include natural compounds isolated from viral, bacterial, fungal, plant and animal sources, as well as synthetic compounds. Neither the source, chemical structure, or mechanism of action of the antimicrobial is critical to this invention. For example, an antimicrobial may alter AarC activity by modifying transcriptional, translational or post-translational mechanisms either singly or in combination.

Several methods are provided herein for using the sequences of the present invention to screen potential antimicrobials which alter AarC biological activity. One method contemplates using bacterial cells which contain chromosomal aarC are transformed with an expression vector which contains both aarC and aac(2')-la nucleotide sequences in either a "dilution test" or a "disc diffusion test." Bacterial cells containing such an expression vector can be generated as described above. In the dilution test, it is preferred that three types of bacterial cell are used. The first cell type contains chromosomal aarC. The second and third cell types contain, in addition to the chromosomal aarC, a single copy or multiple copies of the expression vector respectively. Each of the three cell types is separately contacted with the antimicrobial by inoculating a suspension of each cell type into a series of tubes containing a range of known concentrations of the potential antimicrobial to be tested.

After incubation, antimicrobial activity is detected by determination of the inhibition of visible growth as measured by lack of turbidity. If the compound has no effect at any concentration tested on the growth of any of the three cell types, then the compound is not antimicrobial.

Alternatively, if at a given concentration the potential antimicrobial inhibits the growth of each of the three cell types, then the compound's activity could either specifically target AarC activity, or be independent of AarC. To ascertain whether the potential antimicrobial targets AarC activity, differential growth of bacterial cells which contain a single copy and multiple copies of the expression vector is examined in a series of concentrations (lower than the concentration which resulted in growth inhibition of each of the three cell types) of the potential antimicrobial. If the growth of cells containing a single copy and multiple copies of the vector is equally inhibited at each of the tested concentrations, the potential antimicrobial probably does not target AarC. On the other hand, if growth inhibition by the potential antimicrobial of cells containing a single copy of the vector is greater than the growth inhibition observed in cells containing multiple copes of the vector, the antimicrobial likely targets AarC. This is because the additional AarC polypeptide which is produced by cells containing multicopy vectors would alleviate the inhibition of AarC expressed by a single copy of the vector.

Similarly, if at a given concentration of the potential antimicrobial, growth inhibition is greatest in cells which do not contain the vector, with cells containing a single copy of the vector showing intermediate inhibition and with cells containing multiple vector copies showing the least inhibition, then the antimicrobial likely targets AarC. This is because the increased activity of AarC, which is concomitant with increased plasmid copy number, in cells containing multiple expression vectors alleviates the tested compound's antimicrobial activity In the disc diffusion test, a paper disk containing a specified amount (not concentration) of the antimicrobial to be tested is applied to an agar surface that has been freshly inoculated with bacterial cells which contain either a single copy or multiple copies of an expression vector which expresses both aarC and aac(2')-la nucleotide sequences. The antimicrobial is allowed to diffuse into the medium over an 18- to 24-hour period resulting in a zone of inhibition at the point at which a critical concentration of the antimicrobial inhibits bacterial growth. If a zone of inhibition is observed on plates containing either cells which have a single copy or multiple copies of the expression vector, the antimicrobial probably does not affect AarC activity. On the other hand, if a zone of growth inhibition is observed only on plates in which the bacteria contain a single copy of the expression vector, and not on plates in which the bacteria contain multiple copies of the vector, then the antimicrobial likely targets AarC activity.

Yet other methods are contemplated for screening antimicrobials which alter AarC activity. One embodiment contemplates using bacterial cells which have been transformed with expression vectors which contain aarC and a fusion gene of aac(2')-la and a reporter gene. For example, preliminary screening of antimicrobials can be performed by using bacterial cells which contain an expression vector that expresses aac(2')-lacZ and a single copy of an expression vector which expresses wild type aarC. These cells are grown on an agar surface containing X-Gal and treated either with different amounts of the antimicrobial to be tested or with buffer alone. The formation of blue colonies on plates treated with the antimicrobial, and of white colonies on control plates treated with buffer alone suggests that the antimicrobial alters AarC activity. To confirm that antimicrobial activity targets AarC activity, a secondary screening step is performed. In that step the effect of the antimicrobial is compared using bacterial cells containing an expression vector which expresses aac(2')-lacZ as well as either a single copy or multiple copies of an expression vector which expresses wild type aarC cells. Following parallel treatment of the two cell types with different concentrations of the antimicrobial, and growth on agar containing X-Gal, the color of the rings around the colonies arising from each of the cells is visually compared. If a given concentration of the antimicrobial results in the development of blue rings on plates of cells containing a single copy of the aarC expression vector, and in rings having a relatively reduced blue intensity on plates of cells containing multiple copies of the aarC expression vector, then the test antimicrobial activity likely interferes with AarC activity. This is because the higher concentration of AarC produced by cells containing a multiple copy of an aarC expression vector relative to the AarC concentration produced by cells expressing a single copy of the aarC expression vector would be expected to alleviate the antimicrobial's effect on AarC.

Having screened a potential antimicrobial compound for its effect on AarC, the bacteriostatic and bactericidal activity of the antimicrobial compound can be further examined using techniques well known in the art [Snyder et al., In *Modern Pharmacology*, 2d Ed., C. R. Craig and R. E. Stitzel, (eds.), Little, Brown and Company, Boston, pp. 631–640 (1986); Conte et al., *Manual of Antibiotics and Infectious Diseases*, 6th Ed., Lea and Febier, Philadelphia, pp. 135–152 (1988)]. To determine the compound's bacteriostatic activity in relation to a particular bacterium, a cell suspension of the particular bacterium is introduced into a number of tubes which contain a range of known concentrations of the antimicrobial, usually as an integral power of 2 (e.g., 128 $\mu$g/ml) and decreasing on a $\log_2$ basis (i.e., 64, 32, 16, 8, 4, etc.) to the lowest concentration to be tested. After incubation, the lowest concentration inhibiting visible growth by turbidity is referred to as the minimum inhibitory concentration (MIC). Inhibition of visible bacterial growth indicates bacteriostatic activity.

To assess bactericidal activity, an aliquot is taken from a tube showing bacteriostatic activity as described above, and this aliquot is added to agar plates. If growth occurs, then the agent is bacteriostatic. However, if no growth occurs, the agent is bactericidal. The minimal bactericidal concentration (MBC), which is also referred to as the minimum lethal concentration (MLC), is defined by the lowest concentration of antimicrobial yielding less than or equal to 0.1% survivor organisms from the original inoculum of approximately 100,00 organisms.

The above-described methods of determining bacteriostatic and bactericidal activities have been reviewed [Woods, Infect. Dis. Clin. North. Am. 9(3):463–481 (1995)] and standardized for antimicrobial testing of aerobic and facultatively anaerobic bacteria [National Committee for Clinical Laboratory Standards: *Performance Standards For Antimicrobial Disk Susceptibility Tests: Approved Standard*, 5th ed. NCCLS Document M2–A5. Villanova, Pa., NCCLS (1993); National Committee for Clinical Laboratory Standards. *Methods For Dilution Antimicrobial Susceptibility Tests For Bacteria That Grow Aerobically: Approved Standard*, 3nd ed. NCCLS Document M7–A3. Villanova, Pa., NCCLS, (1993)], anaerobic bacteria [National Committee for Clinical Laboratory Standards: *Methods For Antimicrobial Susceptibility Testing Of Anaerobic Bacteria: Approved Standard*, 3nd ed. NCCLS Document M11–A3. Villanova, Pa., NCCLS (1993)] and for mycobacteria [National Committee for Clinical Laboratory Standards: Antimicobacterial Susceptibility Testing: Proposed Standard. NCCLS Document P24-P. Villanova, Pa., NCCLS (1989)].

IV. Methods For Detecting Microbes Containing The aarC Nucleotide Sequence

The present invention provides methods for the detection of microbes which contain the aarC nucleotide sequence shown in FIG. 2, fragments, variants, derivatives and homologs thereof. Cells which contain the aarC coding sequence may be identified by a variety of procedures know to those of skill in the art. These procedures include, but are not limited to, DNA-DNA or DNA-RNA hybridization as well as amplification (e.g., PCR) using DNA probes (e.g., oligonucleotide or oligomer probes or amplimers), mRNA probes and fragments of the sequence encoding AarC. These probes and fragments can be made using a wide variety of techniques known in the art such as chemical synthesis, restriction digestion and expression of the aarC sequence, or any portion of it, in an expression vector. Labelling of the synthesized or expressed probes and aarC fragments can be achieved using oligolabeling, end-labeling or PCR amplification using a labeled nucleotide.

Having generated labelled probes, microbes present in a sample (e.g., urethral exudate, blood, urine, wound culture, respiratory culture, genital specimen or feces specimen) can be tested for the presence of the aarC sequence using Southern or reverse Northern analysis of isolated plasmid or total cellular DNA, or using Northern analysis of MRNA.

Alternatively, whole-cell lysates of colonies may be used. Colonies can be either grown on filters or spotted onto filters [Moseley et al., J. Infect. Dis. 142:892–898 (1980)] either directly [Perine et al. J. Infect. Diseases 152(1):59–63 (1985)] or following overnight culture [Gootz et al., Antimicrob. Agents and Chemother. 28(1):69–73 (1985)]. Briefly, a solid support such as nitrocellulose paper or a nylon membrane is inoculated with a clinical specimen, or with a broth culture of a clinical specimen suspected of containing bacteria. The cells are lysed onto the nitrocellulose paper and the DNA denatured, for example by treatment with NaOH. The support is treated with pronase and chloroform to lower background non-specific binding of DNA probes to colony material. Prehybridization and hybridization of the filters (ie., support) with oligonucleotides, oligomers, or portions of the aarC sequence is then performed using standard techniques. Hybridization is detected using any one of many available methods, such as by imaging radioactive probes using X-ray films (i.e., autoradiography).

It will be apparent to one skilled in the art that detection of bacteria which harbor the aarC sequence or its homolog in a sample derived from a subject demonstrates that it is beneficial to administer antimicrobials which alter AarC activity to the subject. In addition, such detection also permits monitoring the subject for the presence of the bacteria during and after administration of the antimicrobial.

V. Methods For Detecting Microbes Containing The AarC Polypeptide Sequence

This invention also contemplates the detection of AarC and its variants in bacteria using AarC antibodies. These antibodies include, but are not limited to, polyclonal and monoclonal antibodies. In addition, chimeric antibodies may be produced, for example, by splicing mouse antibody genes to human antibody genes. Single chain antibodies against AarC are also contemplated as well as antibody fragments generated by pepsin digestion of the antibody molecule or by reduction of the disulfide bridges of the Fab fragments.

For the production of AarC antibodies, any antigenic portion of the AarC sequence of FIG. 2 can be used either alone (to produce an antibody against AarC) or fused with amino acids of another protein e.g., glutathione (to produce an antibody against the chimeric molecule). Such antibodies include, but are not limited to, polyclonal, monoclonal, chimeric, single chain, Fab fragments and fragments produced by a Fab expression library. Neutralizing antibodies, ie., those which inhibit dimer formation, are especially preferred for diagnostics and therapeutics.

AarC polypeptide to be used for antibody induction need not retain biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of AarC amino acids may be fused with those of another protein such as keyhole limpet hemocyanin and antibody produced against the chimeric molecule.

For the production of antibodies, various hosts including goats, rabbits, rats, mice, etc may be immunized by injection with Aarc or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and *Corynebacterium parvum* are potentially useful adjuvants.

Monoclonal antibodies to AarC may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al. (1983) Immunol Today 4:72; Cote et al. (1983) Proc Natl Acad Sci 80:2026–2030) and the EBV-hybridoma technique [Cole et al. (1985) *Monoclonal Antibodies and Cancer Therapy*, Alan R Liss Inc, New York N.Y., pp 77–96].

AarC antibodies can be used to detect AarC polypeptide in clinical samples such as body fluids or extracts of cells or tissues using several known techniques such as enzyme-linked immunosorbent assay (ELISA), radioimmunoassay (RIA) and fluorescent activated cell sorting (FACS). Reporter molecules known in the art can be joined to the polypeptides and antibodies to facilitate detection of polypeptide-antibody binding.

BRIEF DESCRIPTION OF THE DRAWINGS

FIG. 2 shows the DNA sequence of a 1345 bp fragment containing the aarC gene (SEQ ID NO:4) and the deduced AarC polypeptide sequence (SEQ ID NO:5).

FIGS. 3A–3C shows an alignment of the nucleic acid sequence of aarC with (A) an open reading frame in *Haemophilus influenzae* (SEQ ID NO:7), (B) gpcE sequence (SEQ ID NO:8) of *E. coli*. The alignment of the anti-sense nucleic acid sequence of aarC (SEQ ID NO:10) with the *Bacillus subtilis* nuleic acid sequence (SEQ ID NO:9) is shown in FIG. 3C.

FIG. 4 depicts a comparison between AarC and GcpE protein sequences.

FIGS. 7A–7B shows two methods for screening compounds for antimicrobial activity.

FIG. 8 shows the nucleotide sequence (SEQ ID NO:12) of the aac(2')-Ia gene and the amino acid sequence (SEQ ID NO: 13) of the encoded Aac(2')-Ia.

EXPERIMENTAL

Figure 1A:
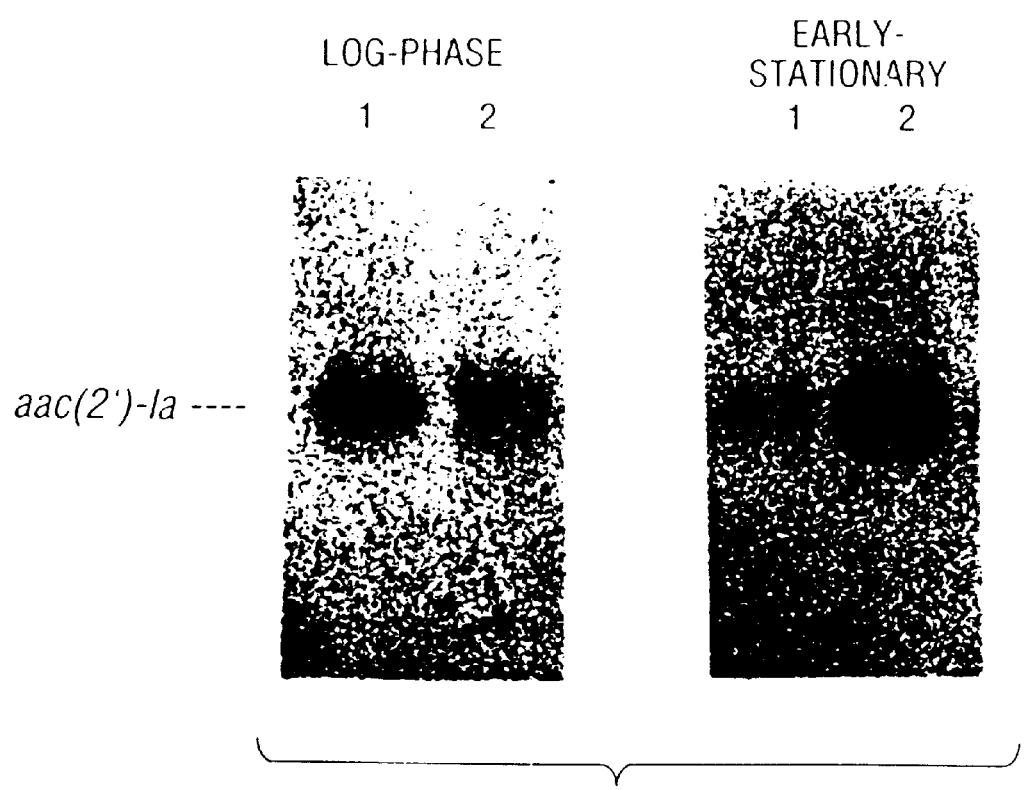
FIGS. 1A and 1B are a Northern blot of mRNA prepared from *P stuartii* cells at log phase and stationary phase showing that mRNA for aac(2')la and aarP is expressed in cells at high cell density.

The following examples serve to illustrate certain preferred embodiments and aspects of the present invention and are not to be construed as limiting the scope thereof.

In the experimental disclosure which follows, the following abbreviations apply: g (gram); L (liter); μg (microgram); ml (milliliter); bp (base pair); ° C. (degrees Centigrade); kb (kilobases); X-gal (5-bromo-4-chloro-3-indolyl-β-D-galactopyranoside); LB (Luria Broth), Boehringer Mannheim (Indianapolis, Ind.); Gibco BRL (Gaithersburg, Md.); Pharmacia Biotech (Piscataway, N.J.); (Stratagene, LaJolla Calif.);

The Examples disclosed hereafter utilize the following bacterial strains, plasmids and growth conditions. The bacterial strains and plasmids used are listed in Tables 1 and 2.

TABLE 1

E. coli Strains

| Strain | Genotype And Relevant Markers | Reference Or Source |
| --- | --- | --- |
| XL1-Blue | recA1 endA1 gyrA96 thi-1 hsdR17 supE44 relA1 Δlac-pro[F¹ proAB lac/$^q$ lacZΔM15 Tn10] | Stratagene |
| DH5α | recA1 endA1 gyrA96 thi-1 hsdR17 supE44 relA1 ΔiacZYA-argFU169 φ80diacZΔM15 | Gibco/BRL |
| DH5α λ pir | DH5α lysogenized with λpir | Macinga et al., J. Bacteriol. 177:3407–3413 (1995) |
| SM10 λpir | thi thr leu tonA lacY supE recA RP4-2-Tc:Mu, Km$^r$ λpir | Miller and Mekalanos, J. Bacteriol. 170:2575–2583 (1988) |
| P. stuartii strains | | |
| PR50 | Wild-type | Rather et al., J. Bacteriol. 175:6492–6498 (1993) |
| PR500 | PR50 containing pR401 and pACYC184.aarG | Described herein |
| PR60 | PR50 aarCl | Described herein |

TABLE 2

Plasmids

| Plasmid | Genotype And Relevant Markers | Reference Or Source |
| --- | --- | --- |
| pACYC184 | Medium copy vector, Cm$^R$, Tc$^R$ | Chang and Cohen, J. Bacteriol. 134:1141–1156 (1978) |
| pKNG101 | R6K derived suicide plasmid containing Str$^R$ and sacB | Kaniga et al., Gene 109:137–141 (1991) |
| pBluescript SK (−) | High copy vector, Ap$^R$ | Stratagene |
| pBCKS (−) | High copy vector, CM$^R$ | Stratagene |
| pR401 | aac(2')-lacZ transcriptional fusion | Rather and Orosz, J. Bacteriol. 176:5140–5144 (1994) |
| pACYC184.aarC | pACYC184 containing 1.7 kb P. stuartii chromosomal fragment. | Described herein |
| pSK-2.0 | pBluescript SK (−)::2.0 kb SalI fragment from pACYC184.aarC | Described herein |
| pSK.aarC1.4 | pBluescript SK (−)::1.4kb SalI-BamHI fragment from pSK-2.0 | Described herein |
| pBC.aarC1.4 | pBCKS(−)::1.4 kb SalI-BamHI fragment from pSK-2.0 | Described herein |
| pSK.aarC1.0 | pBluescript SK (−)::1.0 kb SspI-BamHI fragment from pSK.aarC1.4 | Described herein |
| pBC.aarC1.0 | pBCKS (−)::1.0 SspI-BamHI fragment from pSK.aarC1.4 | Described herein |
| pBC.aarC::lacZ | pBC.aarC1.0::lacZ inserted at unique NruI site. | Described herein |
| pKNG101.aarC::lacZ | pKNG101::4.5 kb SalI-BamHi fragment from pBC.aarC::lacZ | Described herein |
| pSK.aarC5.0 | pBluescript SK (−)::5.0 kb SalI chromosomal fragment from PR50 | Described herein |
| pPR25 | pBluescript SK (−)::0.7 kb NruI fragment from pSK.aarC5.0 | Described herein |
| pPR26 | pBluescript SK (−)::3.9 kb NruI-SalI fragment from pSK.aarC5.0 | Described herein |
| pSK.aarC1.4-mut | pBluescript SK (−)::1.4 kb SalI-BamHI fragment containing aarCl allele | Described herein |
| pSK.aarC1.0-mut | pSK.aarC1.0 with substituted 320 bp NruI-BclI fragment from pSK.aarC1.4mut | Described herein |

*P. stuartii* PR50, previously described by Rather et al. [Rather, P. et al., J. Bacteriol 175:6492–6496 (1993)] is a wild-type strain and was the parent strain for the isolation of all mutants. *E. coli* XL1-blue (Stratagene) and DH5a (Gibco/BRL) were used as hosts for the propagation of plasmids. In addition, to propagate R6K pir-derivatives, strains DH5a λ,pir (Macinga, D. R. et al., J. Bacteriol. 177:3407–3413 (1995) and SM10 λ pir [Miller, V. H. et al., J. Bacteriol. 170:2575–2583 (1988)] were used. Plasmids pACYC184 [Chang, A. C. Y. et al., J. Bacteriol. 134:1141–1156 (1978)], pBluescript SK(−) (Stratagene), pBCKS (−) (Stratagene), and pKNG101 [Kaniga, K. et al., Gene 109:137–141 (1991)] were used as cloning vectors. All bacteria were grown using LB media supplemented with 15 g/L agar as needed. Antibiotics were used at the following concentrations for growth of *E. coli*, ampicillin 150 μg/ml, chloramphenicol 25 μg/ml, streptomycin 25 μg/ml, tetracycline 15 μg/ml, and kanamycin 20 μg/ml. For growth of *P. stuartii*, antibiotics were used at the following concentrations; ampicillin 150 μg/ml, chloramphenicol 100 μg/ml, streptomycin 75 μg/ml and tetracycline 30 μg/ml. Selection for sucrose resistance in *P. stuartii* was done at 30° C. on LB agar plates without NaCl and containing 5% sucrose.

EXAMPLE 1

Identification Of The aarC Gene

The aarC gene was fortuitously isolated in the course of a study of the negative regulators of the chromosomal 2'-N-acetyltransferase (aac(2')-la) gene [Rather et al. (1993) J. Bacteriol. 175:6492–6498] (FIG. 8; SEQ ID NO:12) in *Providencia stuartii*. In FIG. 8, the aac(2')-la coding region begins at position 264 and ends at position 800. The * denotes the aac(2')-la transcriptional start site. The −10 and −35 regions of the putative aac(2')-la promoter are underlined. In addition, relevant restriction sites are underlined at positions 413 and 788 for BclI and at positions 243 and 1149 for TaqI.

The chromosomal 2-'N-acetyltransferase (aac(2')-la) has a role in the O-acetylation of peptidoglycan in *P. stuartii* [Payie et al. J. Bacteriol. 177:4303–4310 (1995)] and also acetylates some aminoglycosides [Chevereau, M. et al., Biochemistry 13:598–603 (1974), Rather, P. et al., J. Bacteriol. 175:6492–6498 (1993), Yamaguchi, M. et al., J. Antibiotics 27:507–515 (1974)]. As a result, *P. stuartii* cells with increased aac(2')-la expression become resistant to higher levels of aminoglycosides [Macinga, D. R. et al., J. Bacteriol. 177:3407–3413 (1995), Macinga, D. R. et al., Mol. Microbiol. 19:511–520 (1996), Rather, P. et al., J. Bacteriol. 175:6492–6498 (1993), Rather, P. N. et al., J. Bacteriol. 176:5140–5144 (1994)].

The identification of the aarC gene involved complementation of a missense allele (aarC1) which caused the accumulation of aac(2')-la mRNA and resulted in a viable but slow growing cell phenotype. This Example involved (a) isolation of the aarC1 allele, (b) cloning and analysis of aarC, and (c) identification of the aarC1 allele.

A. Isolation Of The aarC1 Allele

To identify genes involved in regulating aac(2')-la expression in *P. stuartii*, a two-pronged strategy was employed. First, mutations were generated that simultaneously increased expression of the chromosomal copy of aac(2')-la and of an aac(2')-lacZ fusion present on the previously described plasmid pR401 [Rather, P. N. et al., J. Bacteriol. 176:5140–5144 (1994)]. pR401 is a plasmid pQF50 [Farinha, M. et al., J. Bacteriol. 172:3496–3499 (1990)] derivative containing an 800-bp fragment of the aac(2')-la promoter region fused to lacZ. Second, it was desirable to prevent the reisolation of aarG mutations which alter the regulation of aac(2')-la (Rather, P. N. Unpublished results).

Therefore, strain PR500, which is a derivative of the wild-type *P. stuartii* PR50 [Rather, P. et al., J. Bacteriol. 175:6492–6498 (1993)], was used. PR500 was generated by introducing into PR50 both pR401 (aac(2')-lacZ) and pACYC184.aarG, a compatible pACYC184 derivative containing the aarG gene. PR500 forms white colonies on plates containing X-gal and has levels of aminoglycoside resistance to 4 µg/ml of gentamicin. Selection of mutants was achieved by plating approximately $10^8$ cells of PR500 on LB plates containing 15 µg/ml of gentamicin and X-gal (to select and identify regulatory mutants), ampicillin (150 µg/ml) to maintain pR401 and chloramphenicol (100 µg/ml) to maintain pACYC184.aarG. As observed previously, colonies arose at a frequency of $10^{-6}$–$10^7$ [Rather, P. et al., J. Bacteriol. 175:6492–6498 (1993)]. Colonies which grew under these conditions and exhibited blue color were analyzed further. While not limiting the present invention to any particular mechanism, these colonies presumably resulted from mutations in a trans-acting regulator of aac(2')-la since expression of both the chromosomal copy of aac(2')-la and the plasmid encoded aac(2')-lacZ fusion were increased.

One class of mutants which formed small blue colonies was identified and a representative isolate, PR60, was characterized. Introduction by electroporation (Gene Pulser, Biorad) of the previously cloned aarA, aarB, and aarD genes [Macinga, D. R. et al., Mol. Microbiol. 19:511–520 (1996), Rather, P. et al., J. Bacteriol. 175:6492–6498 (1993), Rather, P. N. et al., J. Bacteriol. 176:5140–5144 (1994)] into PR60 did not result in complementation indicating that PR60 contained a new regulatory mutation which was designated aarC1. PR500 was then cured of pACYC184.aarG by growing the cells in the absence of chloramphenical, resulting in PR60 (aarC1/pR401) which displayed a phenotype identical to PR500, indicating the presence of aarG in multicopy did not alter the effects of the aarC1 mutation.

i) aarC1 Increases aac(2')-la At High Cell Density

To assess the role of the aarC1 mutation on the expression of aac(2')-la, the activity of β-galactosidase and the aac(2')-la mRNA levels were measured in *P. stuartii* cells containing the aarC1 allele and a aac(2')-lacZ fusion on the previously described plasmid pR401 [Rather, P. N. et al., J. Bacteriol. 176:5140–5144 (1994)].

β-galactosidase activity is reported as Miller units [Miller, J. H. Cold Spring Harbor Laboratory, Cold Spring Harbor, N.Y. (1972)] and represents the average of triplicate samples from three independent experiments. The accumulation of β-galactosidase was measured in wild-type PR50/pR401 and in PR60 (aarC1/pR401) which contains the aac(2')-lacZ fusion. An 8.9-fold increase in β-galactosidase accumulation was observed in PR60 (32.1±2.4 Miller units) relative to PR50 (3.6±0.2 Miller units). This experiment was repeated two additional times and gave increases of 8.8 and 9.2-fold respectively in PR60. This provided indirect evidence that aarC1 increased the expression of the aac(2')-la gene.

Northern blot analysis was then used to directly examine the effects of the aarC1 allele on aac(2')-la mRNA accumulation. RNA was prepared from wild-type PR50 and from PR60 (aarC1) cured of plasmid pR401 at log-phase ($OD_{600}$=0.2) and examined by Northern blot analysis as follows. RNA was prepared for Northern blot analysis by using the TRizol reagent (Gibco/BRL) and was fractionated on a 1.2% agarose gel containing 2.2 M formaldehyde and transferred to Nylon membrane by capillary transfer. To insure both equal loading and transfer of RNA to the nylon membrane, RNAs were directly photographed on the nylon filter by UV illumination. Filters were then probed with a digoxigenin labeled 602 bp TaqI-SspI fragment containing the aac(2')-la coding sequence. Filters were developed using LumiPhos 530 (Boehringer Mannheim) and exposed to X-ray film.

Figure 1B:
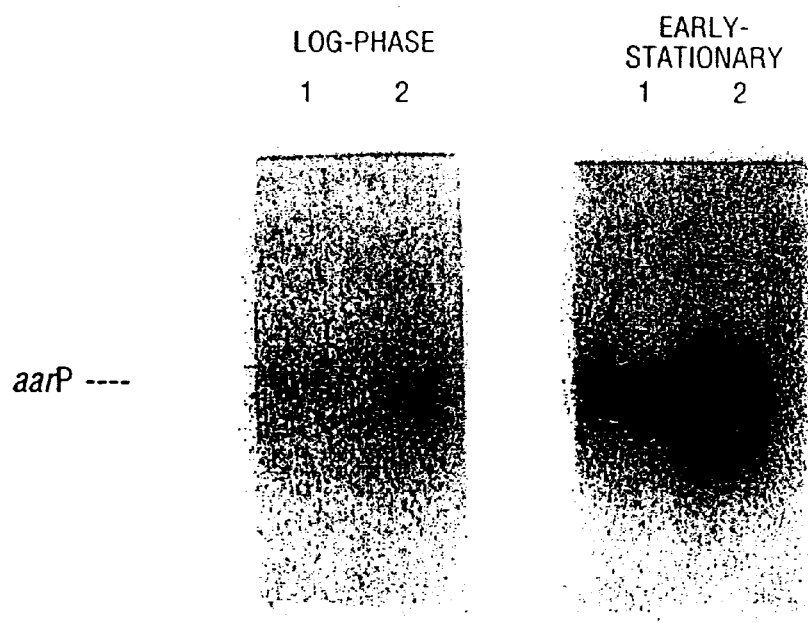

Unexpectedly, the levels of aac(2')-la mRNA accumulation in PR60 (aarC1) were not significantly different from wild-type and in some instances appeared to decrease. Based on this result, the effects of the aarC1 allele on aac(2')-la expression was examined at various stages of growth. RNA was prepared from cells at log phase ($OD_{00}$=1.2) and aac(2')-la mRNA accumulation was examined by Northern Blot analysis, as shown in FIG. 1. FIG. 1 shows Northern blots using total RNA (20 µg) prepared from PR50 (wild-type) or from PR60 (aarC]) cells at early-log ($OD_{600}$ of 0.2) and early stationary phase ($OD_{600}$ of 1.2). Lane 1 represents RNA from PR50 and lane 2 represents RNA from PR60 (aarC1). In FIG. 1A, RNA was probed with a 602 bp TaqI-SspI fragment specific to aac(2')-la. The levels of aac(2')-la mRNA in cells of PR50 (wild-type) and PR60 (aarC1) were approximately equal at log phase (FIG. 1A). However, at late-log/early stationary phase, PR60 demonstrated a considerable increase in the accumulation of aac(2')-la mRNA relative to wild-type PR50. These results show that the aarC1 mutation increases aac(2')-la mRNA levels specifically at late-log/early stationary phase.

ii) Increased Expression Of The Transcriptional Activator aarP In An aarC1 Background The transcriptional activator, AarP, is known to activate the aac(2')-la gene [Macinga, D. R. et al., J. Bacteriol. 177:3407–3413 (1995)]. To determine whether the increased aac(2')-la expression that was observed in the aarC1 background may have resulted from increased aarP expression, the accumulation of aarP mRNA was examined by Northern blot analysis. FIG. 1B shows Northern blots using total RNA (20 μg) prepared from PR50 (wild-type) or from PR60 (aarC1) cells at early-log ($OD_{600}$ of 0.2) and early stationary phase ($OD_600$ of 1.2). Lane 1 represents RNA from PR50 and lane 2 represents RNA from PR60 (aarC1) which was probed with a digoxygenin labeled 0.4 kb PCR generated fragment specific to aarP. At low cell density, the aarC1 allele did not significantly affect the accumulation of aarP mRNA in PR60, relative to wild-type PR50. However, in cells at high density, the accumulation of aarP mRNA was significantly increased in the aarC1 background. These results show that aarC1 allele increases aarP mRNA only in cells at high density.

To further test whether aac(2')-la overexpression in the aarC1 background was simply due to overexpression of aarP, we have attempted to introduce an aarP::Cm disruption into the aarC1 background. However, attempts to construct this double mutant have failed repeatedly.

B. Cloning And Analysis Of aarC

PR60 (aarC1) formed colonies that were considerably smaller than wild-type PR50 after 24 hours of growth. Since the aarC1 mutation was selected spontaneously, a single mutation may be responsible for both the slow growth phenotype and the increased aac(2')-la expression. Therefore, to identify the wild-type aarC gene, aarC was isolated and subcloned by complementation of the aarC1 phenotype (i.e., viable yet slow growing cells) with a library of wild-type *P. stuartii* DNA, and sequenced the aarC gene as follows.

i) Isolation And Subcloning Of aarC

A recombinant library of *P. stuartii* DNA in pACYC184 [Chang, A. C. Y. et al., J. Bacteriol. 134:1141–1156 (1978), Macinga, D. R. et al., J. Bacteriol. 177:3407–3413 (1995)] was introduced by electroporation (Gene Pulser, Biorad) into PR60/pR401 (aarC1/aac(2')-lacZ) and colonies with a normal growth phenotype were isolated. This resulted in the isolation of plasmids with different inserts containing a common region of DNA based on restriction mapping. The resulting transformants now formed white colonies on X-gal plates. In addition, retransformation of a representative plasmid, pACYC184.aarC, demonstrated that the insert *P. stuartii* DNA was responsible for correcting the slow growth phenotype. The fact that both the slow growth phenotype and increased aac(2')-la expression were corrected to wild-type by introduction of the plasmids, suggested that the recombinant plasmids contained the wild-type aarC gene.

The wild-type aarC gene was therefore subcloned using as starting material the previously described Sau3AI recombinant library of *P. stuartii* chromosomal DNA in pACYC184 [Macinga, D. R. et al., J. Bacteriol. 177:3407–3413 (1995)]. Briefly, genomic DNA was isolated and digested with Sau3AI and inserted into pACYC184 which had been digested with BamHI using standard techniques [Sambrook et al.]. Plasmid pACYC184.aarC contains an approximately 1.7 kb Sau3A partial fragment of pR50 chromosomal DNA in pACYC184. Digestion of this plasmid with SalI released a 2.0 kb fragment containing most of the *P. stuartii* insert DNA along with 276 bp of pACYC184 DNA from the BamHI cloning site to of the SalI site. This 2.0 kb SalI fragment was cloned into the SalI site of pBluescript II SK (−) resulting in pSK-2.0. Digestion of pSK-2.0 with BamHI released a 600 bp fragment and subsequent religation of the vector containing fragment resulted in pSK.aarC1.4 which contained a 1.4 insert entirely composed of *P. stuartii* DNA. This 1.4 kb insert was then cloned into pBCKS (−) as a 1.4 kb BamHI-SalI fragment resulting in pBC.aarC1.4. Plasmid pBC.aarC1.4 was further subcloned by digestion with SspI and BamHI which released an approximately 1.0 kb fragment that was subcloned into EcoRV and BamHI digested pBCKS (−) and pBluescript II SK (−). This resulted in pBC.aarC1.0 and pSK.aarC1.0 respectively.

To isolate a DNA fragment containing a full length version of the aarC gene, chromosomal DNA from PR50 was digested with SalI and fragments of 4–6 kb were ligated to pBluescript II SK (−). Southern blot analysis demonstrated that aarC was within an approximately 5 kb SalI fragment. Colony hybridization using a 309 bp EcoRV fragment from pBC.aarC1.4 was used to identify recombinant plasmids containing the 5kb SalI fragment with the full length aarC gene. This plasmid was designated pSK.aarC5.0 and was used to generate subclones pPR25 and pPR26 as follows. Plasmid pPR25 contains an approximately 0.7 kb NruI fragment from pSK.aarC5.0 cloned into the EcoRV site of pBCKS (−). Plasmid pPR26 contains a 3.9 kb NruI-SalI fragment from pSK.aarC5.0 cloned into the EcoRV and SalI sites of pBCKS (−).

ii) Sequencing aarC

The sequence of the aarC coding region was determined as follows. Fluorescein-labelled universal and reverse primers were used to sequence double stranded DNA using the Autoread sequencing kit (Pharmacia). Internal primers were synthesized and used as needed to fill gaps in the contiguous sequence. Label was incorporated into these sequencing reactions using fluorescein-labelled dATP. All sequencing reactions were run analyzed on an A.L.F. automated sequencer (Pharmacia). The entire nucleotide sequence of both strands of the aarC gene and flanking DNA was determined in this manner.

Specific templates for sequencing were generated as follows. Digestion of pBC.aarC1.4 with EcoRV released fragments of 335, 420, 267, 309 and 80 bp each of which was cloned into the EcoRV site of pBluescript II SK (−) and used as sequencing templates. DNA sequence analysis of the insert within pBC.aarC1.4 indicated the presence of a partial open reading frame of 738 bp capable of encoding a protein of 246 amino acids with a truncated carboxy terminus.

To sequence the remainder of the aarC coding region, a 0.5 kb fragment from pACYC184.aarC containing additional 3' coding region was cloned. Sequencing of this 0.5 kb fragment provided an additional 266 nucleotides downstream of the previous sequence. However, a stop codon for this open reading frame had not yet been reached.

To complete the sequence, plasmid pSK.aarC5.0 was isolated containing the entire aarC gene on a 5.0 kb SalI fragment. Custom primers [aarC.p1=5'-CGTAAATCCACCCGAATTT-3') (SEQ ID NO:1); aarC.p6=5'-TGGTCATCGAAGCAATGATT-3') (SEQ ID NO:2); aarC.p4=5'-TGGCCCTCAATGAGCCAG-3') (SEQ ID NO:3)] were then used to finish the DNA sequence analysis. The aarC DNA sequence (SEQ ID NO:4) (which has been assigned GenBank Accession No. U67933) is shown in FIG. 2.

FIG. 2 shows the sequence (SEQ ID NO:4) of a 1345 bp fragment containing the aarC gene. The deduced AarC protein sequence (SEQ ID NO:5) is shown below the corresponding coding region using single letter amino acids symbols. The position of the unique NruI restriction site used to disrupt aarC by insertion of the lacZ gene is underlined at positions 452–457. Protein sequences which were homologous to the polypeptide sequence (SEQ ID NO:5) encoded by the aarC DNA sequence were performed using the BLASTP program from the National Center for Biotechnology Information.

Alignment of the sense and anti-sense nucleic acid sequences of aarC with an open reading frame of *Hemophilus influenzae*, gpcE of *E. coli*, and a nucleic acid sequence of *Bacillus subtilis* is shown in FIG. 3. The top line in each of the alignments shows the aarC sequence. The sense strand of aarC is shown in FIGS. 3A and 3B. FIG. 3C shows the anti-sense strand of aarC. The positions of the nucleic acids of the sense and anti-sense aarC sequences as they correspond to those shown in FIG. 2 are shown at the left and right of the sense and anti-sense aarC nucleic acid sequences. The numbers appearing at the right and left of the lower line represent the nucleotide numbers allocated by GenBank to each of the polynucleotide sequences. Symbols corresponding to (|) represent identical nucleic acids. The aarC sequence showed 74% homology with the *Hemophilus influenzae* open reading frame, 75% homology with the gpcE of *E. coli* sequence, and 55% homology with the minus strand of *Bacillus subtilis*.

The deduced AarC protein sequence (SEQ ID NO:5) (FIG. 2) contained 366 amino acids and exhibited homology (88% identity) over a stretch of 362 amino acids to the GcpE protein (SEQ ID NO:6) of *E. coli* (1) (FIG. 4). FIG. 4 shows the alignment of the deduced amino acid sequences of AarC and GcpE. Symbols corresponding to (|) represent identical amino acids, (:) represents conserved amino acids and a (.) represents amino acids with low similarity. The position of the valine to glycine substitution in the AarC mutant protein described below is indicated at position 136 in FIG. 2.

Analysis of the AarC protein did not reveal any obvious functional motifs. Thus, the mechanism by which it regulates accumulation of aac(2')-la and aarP mRNA remains to be determined. However, hydropathy analysis of AarC did not reveal any obvious signal sequence of hydrophobic regions, suggesting that AarC is cytoplasmic.

In addition, the deduced AarC protein sequence showed a high degree of conservation (86% homology) over 361 amino acids to an open reading frame in the *Haemophilus influenzae* genome [Farinha, M. et al., J. Bacteriol. 172:3496–3499 (1990)]. In addition to homology to protein sequences from gram negative bacteria, the AarC polypeptide was homologous (ie., 51% amino acid identity) to an open reading frame in the gram positive *B. subtilis* bacteria. The high degree of conservation between proteins from three gram negative and one gram positive bacteria suggests that these related proteins are involved in an important function. Thus, these results, and those in the following Examples 2 and 3, demonstrate that aarC is conserved in gram negative and gram positive bacteria, and is required for the viability of *P. stuartii*.

C. Identification Of The aarC1 Allele

Figure 5:
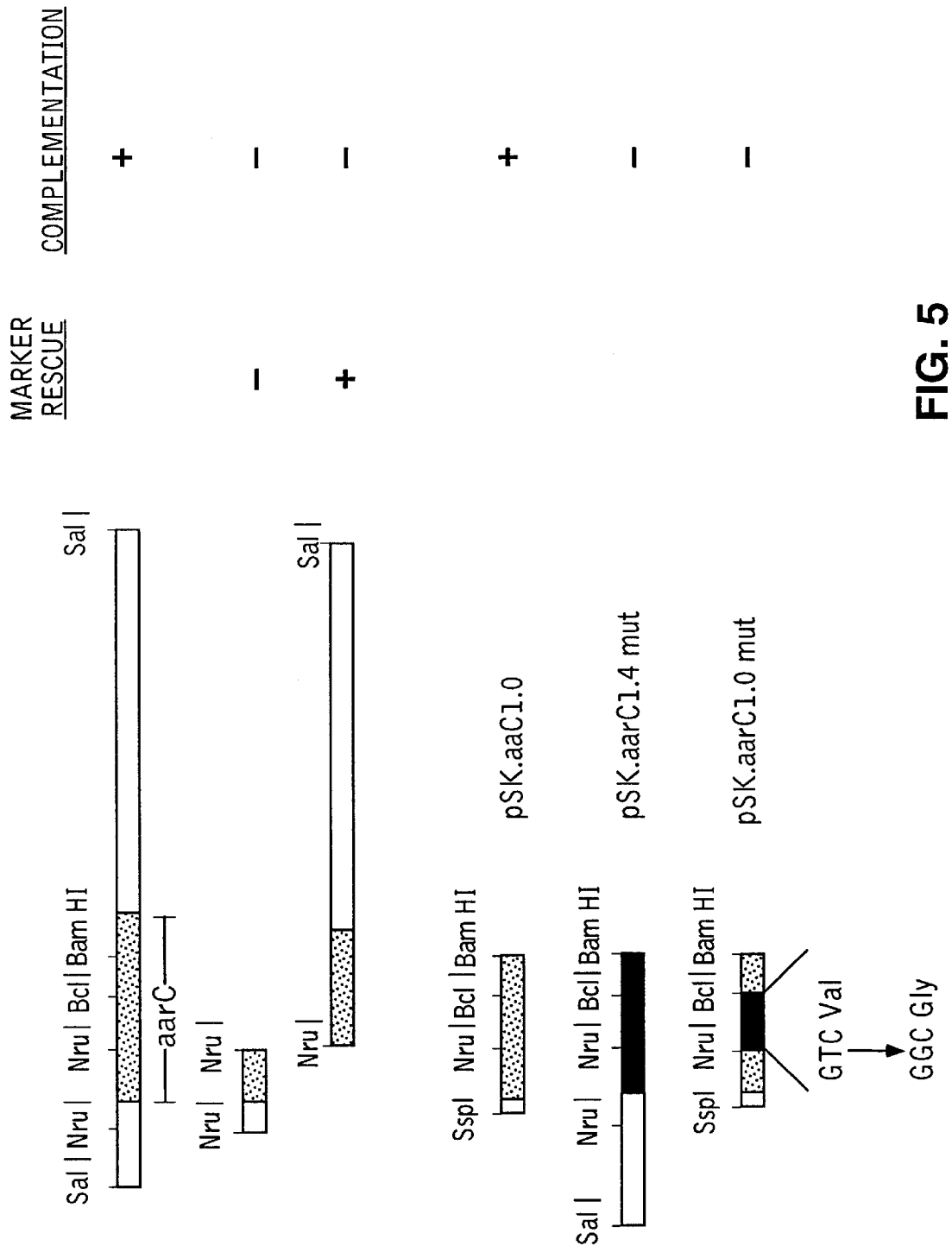
FIG. 5 shows the recombinant plasmids used in mapping the aarC1 allele.

To identify the location of the aarC1 mutation, complementation studies were performed on PR60 cells using different restriction fragments of the aarC gene. FIG. 5 shows the recombinant plasmids containing the aarC region used in these studies. The indicated region represents the portion of the aarC gene present within each plasmid. The ability of each plasmid to complement or marker rescue the aarC1 mutation is shown. A (+) for marker rescue indicates the extensive formation of pappiliae in colonies. A (+) in the complementation column indicates restoration of a wild-type growth rate to the aarC1 mutant.

Plasmid pSK.5.0, which contains the entire aarC gene and flanking DNA on a 5.0 kb SalI fragment was capable of complementing the aarC1 mutation. Subclones of this fragment were generated in pBluescript SK (−) that contained an approximately 700 bp NruI fragment (pPR25) or a 3.9 kb NruI-SalI fragment (pPR26) (FIG. 5). Neither plasmid was capable of complementing the aarC1 mutation when introduced by electroporation (Gene Pulser, Biorad) into PR60. However, PR60 cells containing pPR26 were very unstable and colonies rapidly became papillated with fast growing sectors. In contract, cells containing pPR25 remained small in size. The fast growing cells containing pPR26 could result from correction of the aarC1 allele at high frequency by recombination of pPR26 into the chromosome. Based on these results, the aarC1 mutation was predicted to be downstream of the NruI site.

To further localize the aarC1 mutation, plasmid pSK.aarC1.0 (FIG. 5) containing a 1.0 kb SspI-BamHI fragment was produced. This plasmid partially complemented the aarC1 allele. These results indicated that the aarC1 mutation was likely to reside with the NruI to BamHI interval.

To isolate the aarC1 mutation, chromosomal DNA from PR60 was digested with BamHI and SalI and fragments in the range of 1–2 kb were ligated to pBluescript II SK (−) digested with BamHI and SalI. Colony hybridization with the 309 bp EcoRV fragment from pBC.aarc1.4 was then used to identify plasmids with a 1.4 kb fragment containing the mutant aarC gene. This plasmid was designated pSK.aarCmut.1.4 (FIG. 5). This plasmid failed to complement the aarC1 allele when introduced into PR60. The presence of pSK.aarC1.4mut in either wild-type *P. stuartii* PR50 or in *E. coli* XL1 substantially reduced the growth rate of cells, indicating the mutant AarC gene product may have a dominant negative effect.

To further localize the aarC1 mutation with the 1.4 kb fragment, restriction fragment exchanges were performed between pSK.aarC1.0 and pSK.aarC1.4mut. Substitution of the wild-type 320 bp NruI-BclI fragment of pSK.aarC1.0 with the mutant fragment from pSK.aarC1.4mut resulted in *E. coli* transformants that were slow growing. Furthermore, the resulting hybrid plasmid pSK.aarC1.0mut failed to complement PR60. This indicated that the aarC1 mutation was within this 320 bp NruI-BclI interval. The nucleotide sequence of this fragment revealed a single T to G transversion resulting in a valine to glycine substitution at position 136 of the AarC protein, a position conserved between the *E. coli* (FIG. 4) and *H. influenzae* homologs [Fleishman, R. D. et al., Science 269:496–512 (1995)].

Because the presence of the aarC1 allele on a high copy plasmid was detrimental to the growth of both *P. stuartii* and *E. coli*, these results suggest that the regulatory consequences of the aarC1 allele, which is recessive to wild-type, are the result of loss of AarC function. Without limiting this invention to any partiuclar mecahnism, these results also suggest that AarC functions as a multimer and that overexpression of the mutant subunit interferes with the function of the wild-type subunits.

EXAMPLE 2

*E. coli* gcpE Gene Restores Wild-Type Phenotype To Cells Containing The aarC1 Allele Although the function of *E. coli* GcpE is unknown, it has been proposed to be an essential gene since attempts to disrupt gcpE in *E. coli* were only possible in cells that contained an episomal copy of gcpE [Baker, J. et al., FEMS Microbiolgy Letters 92:175–180 (1992)]. Thus, to test whether the gcpE gene was functionally equivalent to the aarC gene, we introduced the *E. coli* gcpE gene on plasmid pSE401(7) into PR60 aarC1 by electroporation (Gene Pulser, Biorad). This resulted in restoration of wild-type growth levels. This data suggests that, like the gcpE gene, the aarC gene is an essential gene. Furthermore, these results show that AarC and GcpE proteins are functionally equivalent.

EXAMPLE 3

*E. coli* gcpE Gene Allows Construction Of A Viable Cell Containing An aarC::lacZ Disruption A previous report indicated that gcpE was an essential gene in *E. coli* [Baker, J. et al., FEMS Microbiolgy Letters 92:175–180 (1992)]. To assess the role of aarC in *P. stuartii*, this example describes the integration of an aarC::lacZ disruption into the genome of wild-type *P. stuartii*, and an attempted to rescue the resulting non-viable colonies using the gcpE gene as follows.

A. Construction Of An aarC::lacZ Disruption

A promoterless lacZ cassette was inserted into a unique NruI site in the aarC gene (FIG. 2). Plasmid pBC.aarC1.0, which contains a 1.0 kb portion of the aarC coding region was linearized by digestion with NruI which cuts at position 454 within the aarC coding region. A promoterless lacZ cassette was obtained form pQF50 [Farinha, M. et al., J. Bacteriol. 172:3496–3499 (1990)] by digestion with SmaI and ScaI and ligated in the correct orientation relative to pBC.aarC creating an aarC::lacZ transcriptional fusion. A DNA fragment containing this fusion was excised by digestion with BamHI and SalI and cloned into the previously described suicide vector pKNG101 [Kaniga, K. et al. (1991) Gene 109:137–141] creating pKNG101.aarC::lacZ. This plasmid contains a pir dependent origin of replication, a counterselectable sacB gene, and a streptomycin resistance gene. To introduce pKNG101.aarC::lacZ into the *P. stuartii* chromosome, *E. coli* strain SM10 λ pir [Miller, V. H. et al., J. Bacteriol. 170:2575–2583 (1988)] pKNG101.aarC::lacZ was mated to *P. stuartii* strains as described previously [Rather, P. N. et al., J. Bacteriol. 176:5140–5144 (1994)]. Mating mixtures were then plated on LB containing streptomycin (75 μg/ml), tetracycline (30 μg/ml) and X-gal. In the case of *P. stuartii* strains containing plasmid DNA, ampicillin was also added at a concentration of 300 μg/ml. Selection for loss of the integrated pKNG101.aarC::lacZ was achieved by growth at 30° C. on LB plates without NaCl and containing 5% sucrose.

Figure 6A:
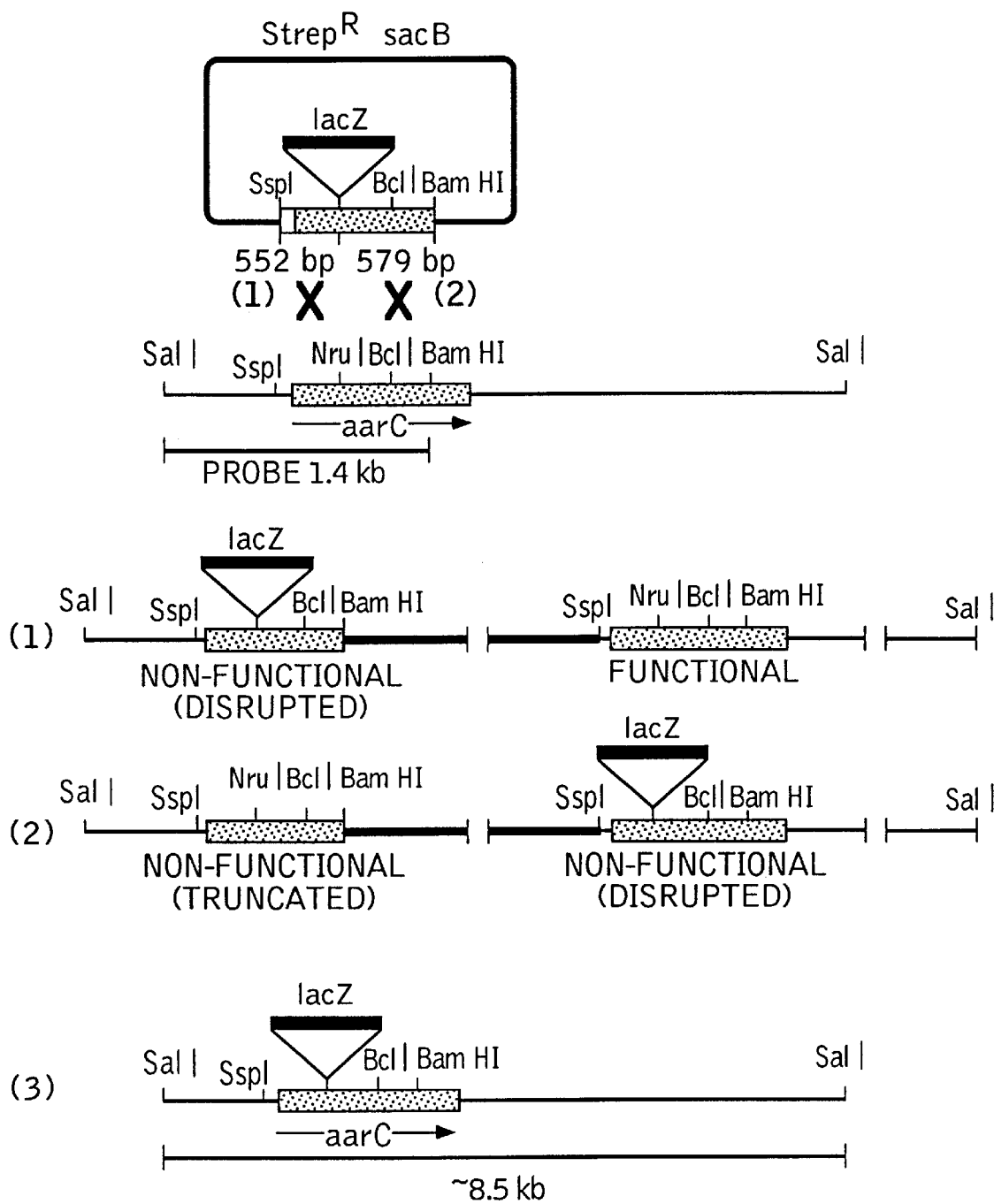
FIGS. 6A–6C depicts the integration of the pKNG101.aarC::lacZ disruption into the chromosome and shows a Southern blot verification of the aarC::lacZ disruption.

The integration of pKNG101.aarC::lacZ into the PR50 chromosome resulted in streptomycin resistant ($Sm^R$) and sucrose sensitive ($suc^S$) colonies which were blue in the presence of X-gal. Integration of pKNG101.aarC::lacZ could occur by either of two crossovers (FIG. 6A) and would result in a strain diploid for aarC. FIG. 6 A depicts plasmid pKNG101.aarC::lacZ at the top and the 5.0 kb SalI chromosomal region of PR50 containing aarC is shown immediately below. Integration of pKNG101.aarc::lacZ into the chromosome can occur within the 552 bp interval 5' to the inserted lacZ cassette as depicted in crossover 1 or within the 579 bp interval 3' to the inserted lacZ cassette as depicted in crossover 2. The predicted structure of the chromosomal region in a strain containing an aarC:lacZ disruption is shown in panel 3. The probe used for Southern blot analysis was the 1.4 kb SalI-BamHI fragment depicted below the PR50 chromosomal region. Crossover 1 would yield a functional copy of aarC. However, crossover 2 would result in two nonfunctional copies of aarC, one with a truncation and one containing the lacZ disruption.

To determine which cross over was present, Southern blot analysis was performed on strains by digestion of chromosomal DNA with SalI followed by transfer to nylon membrane. The aarC probe contained a 1.4 kb BamHI-SalI fragment. The probe specific for lacZ was a 3.2 kb Pst1 fragment from pM C1871 (Pharmacia). Southern blot analysis of 28 SmRSucS blue colonies demonstrated they all contained pKNG101.aarC::lacZ integrated by crossover 1 and thus retained a functional copy of aarC. This was unexpected as there is more homology for crossover 2 (579 bp vs. 552 bp for crossover 1). Excision of the integrated plasmid by selection on 5% sucrose failed to yield blue colonies corresponding to the aarC::lacZ disruption. These results were obtained in two independent experiments, suggesting that colonies containing the aarC::lacZ disruption were not viable.

B. Complementation Of The aarC::lacZ Disruption With The gcpE Gene

Figure 6B:
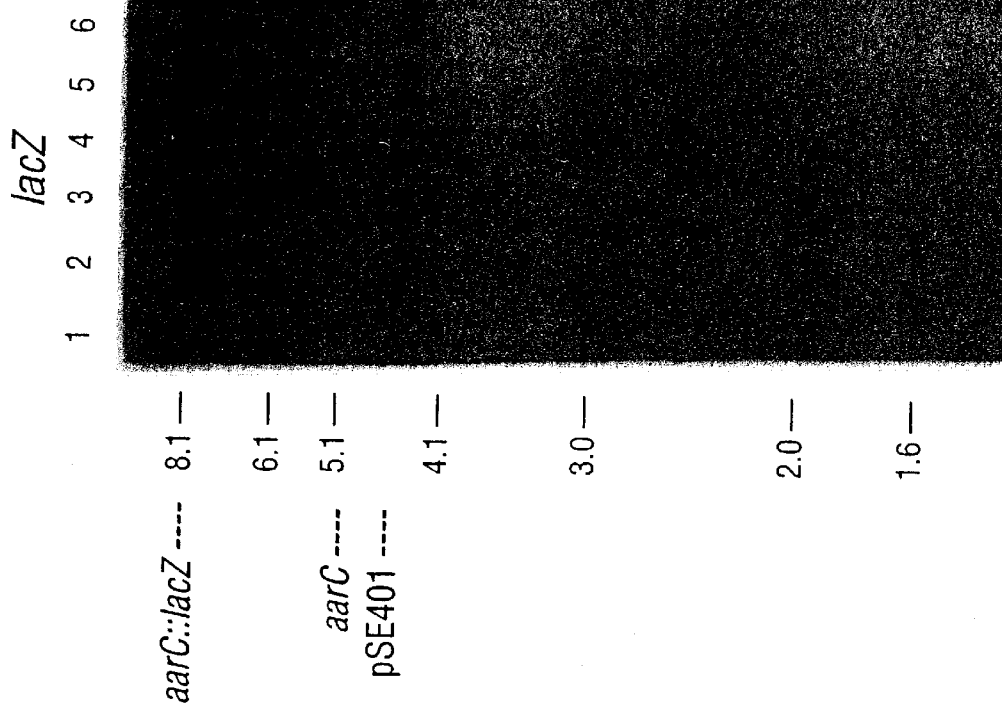
Figure 6C:
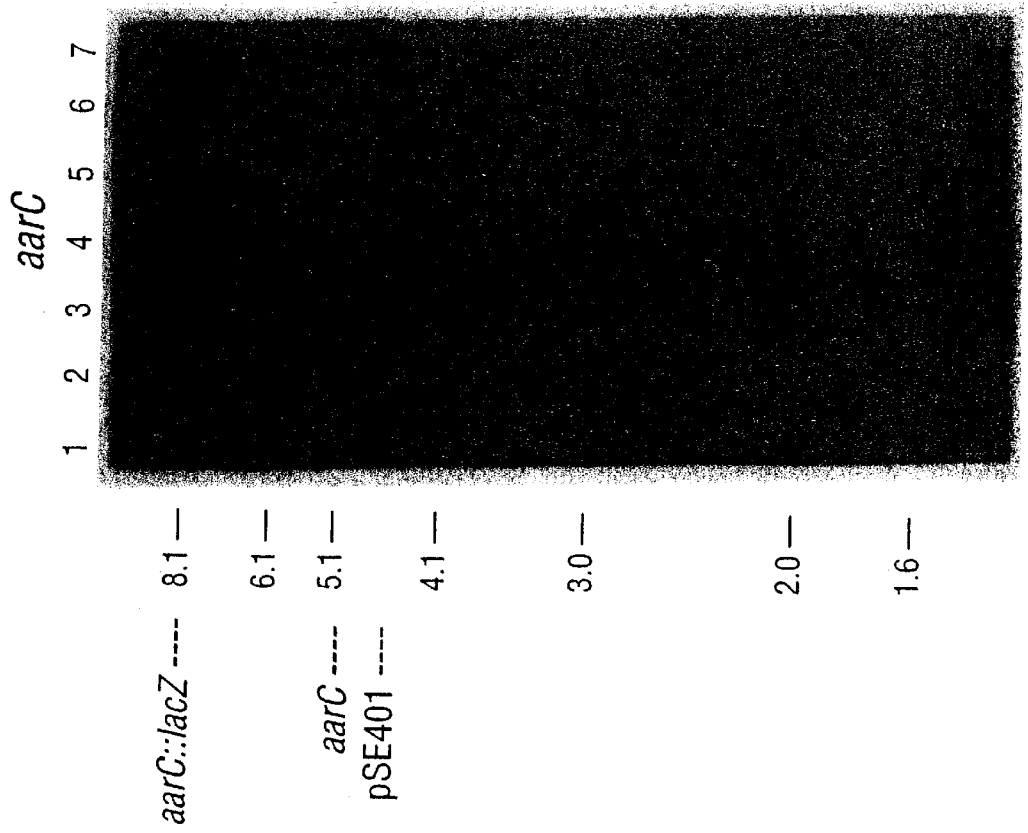

To further test the possibility that colonies containing the aarC::lacZ disruption were not viable, we attempted to resolve the integrated copy of pKNG101.aarC::lacZ in PR50 transformed with plasmid pSE401 containing the *E. coli* gcpE gene [Eisenbeis, S. J. et al., Mol. Gen. Genet. 183:115–122 (1981)]. The gcpE gene was chosen because it was previously shown to complement the growth defect in PR60 (aarC1), and the use of this gene should limit the potential problem of recombinational rescue of the aarC.::lacZ disruption. Selection for sucrose resistance in this strain resulted in approximately equal numbers of blue and white colonies. Southern blot analysis of 5 randomly chosen blue colonies confirmed the presence of the aarC::lacZ disruption as demonstrated in FIG. 6B and 6C. In FIG. 6B and 6C, the Southern blot verification of the aarC::lacZ disruption is shown. All DNAs were digested with SalI. Panel B represents DNA probed with aarC. Lane 1 contains purified pSE401 plasmid DNA, lane 2 contains PR50/pSE401, and lanes 3–7 contain putative PR50 aarC::lacZ/pSE401 mutants. Panel C represents DNA probed with the lacZ gene. All DNAs were digested with SalI. Lane 1 contains PR50/pSE401, and lanes 2–6 contain putative PR50 aarC:lacZ/pSE401 mutants.

When a 1.4 kb SalI-BamHI aarC fragment which is specific to aarC was used, a SalI fragment of 5 kb was present in PR50/pSE401 which corresponded to the aarC locus (FIG. 6B, lane 2). In addition, cross-hybridization was seen with a fragment from pSE401 (FIG. 6B, lanes 1–7). In the 5 putative aarC::lacZ mutants the 5.0 kb SalI fragment was no longer present and was replaced with a fragment of approximately 8.5 kb in size (FIG. 6B lanes 3–7). This was the expected size as the lacZ cassette inserted into aarC was approximately 3.5 kb. To confirm this, a 3.2 kb PstI fragment from pMC1871 (Pharmacia) which is specific for specific for lacZ was used as probe and the 5 putative aarC::lacZ mutants demonstrated hybridization to the same 8.5 kb fragment (FIG. 6C, lanes 2–6). No hybridization was detected with DNA from PR50/pSE401 (FIG. 6C, lane 1).

To determine if the viability of a strain with the aarC::lacZ disruption was now dependent on the presence of pSE401, we grew PR50 (aarC.::lacZ)/pSE401 in the absence of ampicillin for approximately 12 generations then plated the cells to obtain single colonies on LB plates. All resulting colonies (474/474 tested) remained ampicillin resistant indicating that they retained pSE401. In contrast, strain PR50 pKNG101.aarC::lacZ/pSE401 which is diploid for aarC (FIG. 6) was cured of pSE401 at frequencies above 50% under these same conditions. Thus, these results show that the presence of gcpE on pSE401 was essential for the construction of an aarC::lacZ disruption in the chromosome, and that the resulting strain required pSE401 for viability. Furthermore, these results confirm the data from Example 2 which suggest that the *E. coli* GcpE can functionally substitute for AarC.

EXAMPLE 4

Screening Compounds For Antimicrobial Activity

A dilution test and/or disc diffusion test (FIG. 7) is used to determine whether a compound has antimicrobial activity in a bacteria which express AarC. Where potential antimicrobial acitivty which targets AarC activity in *P. stuartii* is investigated three cell types can be used. Control cells are *P. stuartii* cells which contain only chromosomal aarC. The second cell type is *P. stuartii* cells which contain a single copy of an expression vector which contains both aarC and aac(2')-la nucleotide sequences. The third cell type is *P. sturatii* cells which contain multiple copies of the aarC/aac (2')-la expression vector.

A. Dilution Test

In one embodiment of the screening method, a suspension of each of the three cell types is inoculated into a series of tubes containing a range of concentrations of the potential antimicrobial to be tested, e.g., 128 μg/ml, 64 μg/ml, 32 μg/ml, 16 μg/ml, 8 μg/ml, 4 μg/ml, etc.)

After incubation, inhibition of visible growth as measured by lack of turbidity is determined e.g. visually or using photometric methods. FIG. 7 depicts expected results as exemplified using *P. stuartii* cells containing a single copy of the aarC/aac(2')-la expression vector following treatment with a compound which is antimicrobial (FIG. 7A) and a compound which is not antimicrobial (FIG. 7B). If the compound has no effect at any concentration tested on the growth of any of the three cell types (FIG. 7B), then the compound is not antimicrobial.

Alternatively, if at a given concentration the potential antimicrobial inhibits the growth of each of the three cell types (FIG. 7A), then the compound's activity could either specifically target AarC activity, or be independent of AarC. To ascertain whether the potential antimicrobial targets AarC activity, differential growth of bacterial cells which contain a single copy and multiple copies of the expression vector is examined in a series of concentrations (lower than the concentration which resulted in growth inhibition of each of the three cell types) of the potential antimicrobial. If the growth of cells containing a single copy and multiple copies of the vector is equally inhibited at each of the tested concentrations, the potential antimicrobial probably does not target AarC. On the other hand, if growth inhibition by the potential antimicrobial of cells containing a single copy of the vector is greater than the growth inhibition observed in cells containing multiple copes of the vector, the antimicrobial likely targets AarC. This is because the additional AarC polypeptide which is produced by cells containing multicopy vectors would alleviate the inhibition of AarC expressed by a single copy of the vector.

Similarly, if at a given concentration of the potential antimicrobial, growth inhibition is greatest in cells which do not contain the vector, with cells containing a single copy of the vector showing intermediate inhibition and with cells containing multiple vector copies showing the least inhibition, then the antimicrobial likely targets AarC. This is because the increased activity of AarC, which is concomitant with increased plasmid copy number, in cells containing multiple expression vectors alleviates the tested compound's antimicrobial activity B. Disc Diffusion Test In the disc diffusion test, a paper disk containing a specified amount (not concentration) of the antimicrobial to be tested is applied to an agar surface that has been freshly inoculated with bacterial cells which contain either a single copy or multiple copies of an expression vector which expresses both aarC and aac(2')-la nucleotide sequences. The antimicrobial is allowed to diffuse into the medium over an 18- to 24-hour incubation period, during which time the culture is kept at a temperature which is optimum for the growth of the organisms and/or the testing conditions. This results in the formation of a zone of inhibition around the disc, at the point at which a critical concentration of the antimicrobial inhibits bacterial growth. FIG. 7 depicts expected results as exemplified using *P. stuartii* cells containing a single copy of the aarC/aac(2')-la expression vector following treatment with a compound which is antimicrobial (FIG. 7A) and a compound which is not antimicrobial (FIG. 7B). If a zone of inhibition is not observed with either cell type (FIG. 7B), then the compound is not antimicrobial. On the other hand, if a zone of inhibition is observed on plates containing either cells which have a single copy or multiple copies of the expression vector, the antimicrobial probably does not affect AarC activity. On the other hand, if a zone of growth inhibition is observed only on plates in which the bacteria contain a single copy of the expression vector (FIG. 7A), and not on plates in which the bacteria contain multiple copies of the vector, then the antimicrobial likely targets AarC activity.

C. Growth Inhibition Of Cells Containing A aac(2)-lacZ Fusion Gene

This method uses bacterial cells which have been transformed with an expression vector which contains both aarC and a fusion gene of aac(2')-la and a reporter gene. For example, bacterial cells containing an expression vector which expresses aarC and aac(2')-lacZ are grown on an agar surface containing X-Gal and treated either with different amounts of the antimicrobial to be tested or with buffer alone. The formation of blue colonies on plates treated with the antimicrobial, and of white colonies on control plates treated with buffer alone suggests that the antimicrobial alters AarC activity. To confirm that antimicrobial activity targets AarC activity, cells from the blue colonies can be further tested by transfection with a plasmid which expresses wild-type aarC followed by growing the transfected cells on agar containing X-Gal. If the cells form white colonies, the antimicrobial activity does not target the activity of AarC. If blue colonies are formed, the tested antimicrobial activity interferes with AarC activity.

EXAMPLE 5

Measuring Bacteriostatic And Bactericidal Activities

Bacteriostatic and bactericidal activity of the antimicrobial compound are examined using techniques well known in the art [Snyder et al., In *Modern Pharmacology*, 2d Ed., C. R. Craig and R. E. Stitzel, (eds.), Little, Brown and Company, Boston, pp. 631–640 (1986); Conte et al., *Manual of Antibiotics and Infectious Diseases*, 6th Ed., Lea and Febier, Philadelphia, pp. 135–152 (1988)].

A. Bacteriostatic Activity

To determine the compound's bacteriostatic activity in relation to a particular bacterium, a cell suspension of the particular bacterium is introduced into a number of tubes which contain a range of known concentrations of the antimicrobial, usually as an integral power of 2 (e.g., 128 µg/ml) and decreasing on a $log_2$ basis (i.e., 64, 32, 16, 8, 4, etc.) to the lowest concentration to be tested. Inhibition of visible bacterial growth indicates bacteriostatic activity. After incubation, the lowest concentration inhibiting visible growth by turbidity is referred to as the minimum inhibitory concentration (MIC). FIG. 7A shows the MIC of the antimicrobial is 8 µg/ml.

B. Bactericidal Activity

To assess bactericidal activity, an aliquot is taken from a tube showing bacteriostatic activity as described above, and this aliquot is added to agar plates. If growth occurs, then the agent is bacteriostatic. However, if no growth occurs, the agent is bactericidal. The minimal bactericidal concentration (MBC), which is also referred to as the minimum lethal concentration (MLC), is defined by the lowest concentration of antimicrobial yielding less than or equal to 0.1% survivor organisms from the original inoculum of approximately 100,00 organisms.

The above-described methods of determining bacteriostatic and bactericidal activities have been standardized for antimicrobial testing of aerobic and facultatively anaerobic bacteria [National Committee for Clinical Laboratory Standards: *Performance standards for antimicrobial disk susceptibility tests*, 4th ed. Tentative Standard. NCCLS publication M2–T4. Villanova, Pa., NCCLS (1988); National Committee for Clinical Laboratory Standards. *Methods for dilution antimicrobial susceptibility tests for bacteria that grow aerobically*, 2nd ed. Tentative Standard. NCCLS publication M7–T2. Villanova, Pa., NCCLS, (1988)], anaerobic bacteria [National Committee for Clinical Laboratory Standards: *Methods for antimicrobial susceptibility testing of anaerobic bacteria: Approved Standard*, 2nd ed. Publication M11–A2. Villanova, Pa.: NCCLS, 10(15) (1990)] and for mycobacteria [National Committee for Clinical Laboratory Standards: Antimycobacterial *susceptibility testing. Proposed standard.* Publication M24–P. Villanova, Pa.: NCCLS.

EXAMPLE 6

Production Of AarC Antibodies

AarC substantially purified using polyacrylamide gel electrophoresis (PAGE) (Sambrook, supra) is used to immunize suitable animals (e.g., rabbits, hamsters, rats, mice, goats, sheep, etc.) and to produce antibodies using standard protocols (alternatively, recombinant AarC fusion proteins may be purified by affinity or metal chelation chromatography and used to immunize animals). The amino acid sequence translated from AarC is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel FM et al. (supra).

Typically, the oligopeptides are 15 residues in length, synthesized using an Applied Biosystems Peptide Synthesizer Model 431 A using fmoc-chemistry, and coupled to keyhole limpet hemocyanin (KLH, Sigma) by reaction with M-maleimidobenzoyl-N-hydroxysuccinimide ester (MBS; Ausubel FM et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

Purified AarC (native or fusion proteins) may be used to generate antibodies which react specifically with the AarC protein. The production of both polyclonal and monoclonal antibodies utilize techniques standard to the art. Polyclonal antibodies contain a mixture of different types of antibodies that are specific for many different antigens present on the immunogen. Monoclonal antibodies contain a single species of antibody having a defined specificity.

Briefly, polyclonal antibodies are generated by immunization of a host animal with a purified protein. The serum of the immunized animal will contain antibodies directed against one or more epitopes of the injected protein. When rabbits are used for the production of polyclonal antibodies specific for AarC, 50 to 1000 µg of purified AarC is mixed with complete Freund's or another suitable adjuvant and administered subcutaneously (s.c.) to the rabbit. Typically, multiple s.c. injections, each containing a maximum volume of about 400 µl are administered (up to approximately 10 injections may be performed per animal). Alternatively, the immunogen may administered by intramuscular or intradermal injection. Four to six weeks following the initial or primary injection, secondary or booster injections are administered (these may utilize incomplete Freund's or another suitable adjuvant). Additional boosts are given in 4–6 week intervals following the last injection. Immunized rabbits are bled (e.g., using the marginal ear vein) and the serum is screened for the presence of antibodies which react specifically with AarC (e.g., by ELISA screening).

Immunization of mice is conducted as described above with the exception that the dose of antigen is 10–50 µg per injection (250 µl antigen solution mixed with 250 µl complete Freund's adjuvant) and injection is given intraperitoneally (i.p.). The first boost is given two weeks later and employs incomplete Freund's adjuvant; subsequent boosts are given at about 3 week intervals. Serum is collected from the immunized mice (e.g., by tail bleeding) and is screened for the presence of antibodies which react specifically with AarC (e.g., by ELISA screening).

Monoclonal antibodies are produced by immunizing a host animal with purified AarC protein (native or fusion). Once the host has produced antibodies specific for AarC protein, the spleen of the host is removed. The plasma cells present in the spleen of the immune host are then fused with a myeloma cell (the "fusion partner") to produce hybridoma cells. When mice are immunized for the production of plasma cells to be used to generate hybridomas, suitable fusion partners include the X63Ag8.653, Sp2/0-Ag14, FO, NSI/1-Ag4-1, NSO/1 and FOX-NY cell lines [*Antibodies: A Laboratory Manual*, Harlow and Lane, Eds. (1988) Cold Spring Harbor Laboratory Press, Cold Spring Harbor, N.Y., p. 144]. When rats are immunized for the production of plasma cells to be used to generate hybridomas, suitable fusion partners include the YB2/0 and IR983F cell lines (Harlow and Lane, supra). Mice or rats are immunized as described above. Following the generation of specific anti-AarC antibodies in the animals (typically following 2 to 3 booster injection and about 56 days following the initial injection), spleens are removed and splenocytes are fused (e.g., using polyethylene glycol) with the desired fusion partner. The fused cells are diluted in the appropriate selective medium and plated in multiwell culture plates. Each hybridoma cell produces a single type of antibody. Culture supernatant from individual hybridoma cells (removed from the hybridomas about 1 week following plating) is screened using standard techniques to identify those hybridoma cells expressing monoclonal antibodies reactive with AarC (see Harlow and Lane, supra for a review of screening techniques).

When a fusion protein is utilized for the production of antibodies, the resulting antibodies may contain antibodies directed against the fusion partner (e.g., GST). These anti-fusion partner antibodies may be removed from polyclonal sera by chromatography of the sera on a column containing the fusion partner immobilized to a solid support such as Sepharose beads (Pharmacia). For example, to remove anti-GST antibodies from polyclonal sera raised against a GST fusion protein, the sera are chromatographed on a resin comprising the GST protein covalently linked to glutathione Sepharose. Anti-fusion partner antibodies may be excluded during the routine screening of hybridomas during the production of monoclonal antibodies.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, microbiology and related fields are intended to be within the scope of the following claims.

What is claimed is:

1. A method, comprising:
   a) providing, in any order:
      i) a first sample of bacteria, transfected with a recombinant expression vector comprising a nucleic acid sequence that encodes the AarC protein of SEQ ID NO:5; under conditions such that AarC protein is produced from said recombinant expression vector;
      ii) a second sample of bacteria, transfected with a recombinant expression vector comprising a nucleic acid sequence that encodes the AarC protein of SEQ ID NO:5; wherein said second sample comprises more recombinant expression vectors per bacteria cell than said first sample, under conditions such that more AarC protein is produced from said recombinant expression vectors than is produced in said first sample; and
      iii) a compound suspected of having antimicrobial activity;
   b) contacting said first and second samples of bacteria with said compound under conditions such that antimicrobial activity can be detected; and
   c) comparing the level of said antimicrobial activity of said compound on said first and second samples such that the ability of said compound to interfere with the activity of said AarC protein is determined.

2. The method of claim 1, wherein said antimicrobial activity is bacteriostatic.

3. The method of claim 1, wherein said antimicrobial activity is bactericidal.

4. The method of claim 1, wherein said first and second samples of bacteria are gram negative.

5. The method of claim 4, wherein said gram negative bacteria is *Escherichia coli*.

6. The method of claim 1, wherein said first and second samples of bacteria are gram positive.

7. The method of claim 6, wherein said gram positive bacteria is *Bacillus subtilis*.

8. The method of claim 1, further providing a third sample of bacteria, wherein said third sample contains chromosomal aarC.

9. A method, comprising:
a) providing, in any order:
  i) bacteria containing a recombinant expression vector, wherein said vector comprises a fusion sequence comprising a reporter sequence operably linked to aac(2')-Ia and a nucleic acid sequence that encodes the AarC protein of SEQ ID NO:5; and
  ii) a compound suspected of altering AarC activity;
b) contacting said bacteria with said compound, and
c) determining if said compound alters AarC activity.

10. The method of claim 9, wherein said compound is determined to alter AarC activity by causing said bacteria to express said reporter sequence.

11. The method of claim 9, wherein said reporter sequence is a β-galactosidase sequence.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

CGTAAATCCA CCCGAATTT                                                    19

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

TGGTCATCGA AGCAATGATT                                               20

(2) INFORMATION FOR SEQ ID NO:3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

TGGCCCTCAA TGAGCCAG                                                     18

(2) INFORMATION FOR SEQ ID NO:4:

(i) SEQUENCE CHARACTERISTICS:
      (A) LENGTH: 1345 base pairs
      (B) TYPE: nucleic acid
      (C) STRANDEDNESS: double
      (D) TOPOLOGY: linear -continued (ii) MOLECULE TYPE: DNA (genomic)

(ix) FEATURE:
      (A) NAME/KEY: CDS
      (B) LOCATION: 175..1272
      (D) OTHER INFORMATION: /gene= "aarC"
          /note= "Similar to E. coli GcpE protein listed
          by GenBank."

(xi) SEQUENCE DESCRIPTION: SEQ ID NO:4:

| | |
|---|---|
| TTAAAAATAC CTGAAGCATA AAGTCACAAA TTAAGAAGAC GCAAACTGTA TCCTAAAACT | 60 |
| AGAATTGTGA TAGTTTGCAG TTTGCGTTTT TGTGTATAGT GGTCATCGAA GCAATGATTA | 120 |
| TCAACTACAC AACAGTGTTT AAGAGCACAT GGATGTCCAG AGAGTAAAAT TAAA ATG | 177 |
|                                                                                                   Met<br>                                                                                                   1 | |

```
CAT AAT GAA TCA CCG ATA AAA AGA CGT AAA TCC ACC CGA ATT TAT GTA      225
His Asn Glu Ser Pro Ile Lys Arg Arg Lys Ser Thr Arg Ile Tyr Val
            5                  10                  15

GGT AAC GTG CCT ATT GGC GAT GGT GCT CCC ATT GCT GTC CAA TCT ATG      273
Gly Asn Val Pro Ile Gly Asp Gly Ala Pro Ile Ala Val Gln Ser Met
        20                  25                  30

ACG AAT ACG CGC ACG ACG GAT GTT GAA GCC ACT GTG CGG CAA ATC CAA      321
Thr Asn Thr Arg Thr Thr Asp Val Glu Ala Thr Val Arg Gln Ile Gln
    35                  40                  45

TCA CTT GAG CGT GTA GGT GTT GAT ATC GTC CGC GTG TCT GTT CCT ACG      369
Ser Leu Glu Arg Val Gly Val Asp Ile Val Arg Val Ser Val Pro Thr
 50                  55                  60                  65

ATG GAT GCA GCA GAA GCC TTT AAA TTA ATT AAG CAG CGC GTG AAT GTG      417
Met Asp Ala Ala Glu Ala Phe Lys Leu Ile Lys Gln Arg Val Asn Val
                70                  75                  80

CCA TTG GTT GCG GAT ATT CAC TTT GAC TAC CGT ATC GCG ATG AAA GTG      465
Pro Leu Val Ala Asp Ile His Phe Asp Tyr Arg Ile Ala Met Lys Val
            85                  90                  95

GCT GAA TAT GGT GTT GAC TGC CTA CGA ATT AAC CCA GGT AAT ATC GGC      513
Ala Glu Tyr Gly Val Asp Cys Leu Arg Ile Asn Pro Gly Asn Ile Gly
       100                 105                 110

AGT GAA GAG CGT ATT CGC CAA GTC GTT GAT AGT GCT CGT CAT CAC AAC      561
Ser Glu Glu Arg Ile Arg Gln Val Val Asp Ser Ala Arg His His Asn
   115                 120                 125

ATT CCT ATC CGT ATA GGG GTC AAT GGC GGG TCA CTG GAA AAA GAT ATC      609
Ile Pro Ile Arg Ile Gly Val Asn Gly Gly Ser Leu Glu Lys Asp Ile
130                 135                 140                 145

CAA GAA AAA TAC GGT GAG CCA ACA CCT GAA GCA TTG GTT GAA TCA GCA      657
Gln Glu Lys Tyr Gly Glu Pro Thr Pro Glu Ala Leu Val Glu Ser Ala
               150                 155                 160

ATG CGA CAT GTT GAT ATC TTG GAC AGG CTG AAT TTC GAT CAG TTC AAG      705
Met Arg His Val Asp Ile Leu Asp Arg Leu Asn Phe Asp Gln Phe Lys
           165                 170                 175

GTC AGT GTT AAA GCG TCG GAT GTC TTT CTT GCC GTC GGC TCT TAT CGT      753
Val Ser Val Lys Ala Ser Asp Val Phe Leu Ala Val Gly Ser Tyr Arg
       180                 185                 190

TTA TTG GCG CAA AAA ATT GAT CAA CCA CTT CAC CTC GGT ATT ACA GAA      801
Leu Leu Ala Gln Lys Ile Asp Gln Pro Leu His Leu Gly Ile Thr Glu
   195                 200                 205

GCG GGT GGG GCT CGT TCT GGT TCA GTG AAA TCA GCA ATT GGT CTT GGT      849
Ala Gly Gly Ala Arg Ser Gly Ser Val Lys Ser Ala Ile Gly Leu Gly
210                 215                 220                 225

ATG TTG TTG GCT GAA GGT ATC GGC GAT ACG TTA CGT ATC TCA CTC GCG      897
Met Leu Leu Ala Glu Gly Ile Gly Asp Thr Leu Arg Ile Ser Leu Ala
               230                 235                 240
```

```
GCA GAT CCT GTT GAG GAA GTG AAA GTC GGT TTT GAT ATT CTA AAA TCG      945
Ala Asp Pro Val Glu Glu Val Lys Val Gly Phe Asp Ile Leu Lys Ser
            245                 250                 255

TTA CGG ATC CGC TCA CGT GGC ATC AAC TTT ATT GCT TGC CCA ACC TGT      993
Leu Arg Ile Arg Ser Arg Gly Ile Asn Phe Ile Ala Cys Pro Thr Cys
            260                 265                 270

TCA CGC CAA GAA TTT GAT GTG ATT GGT ACG GTA AAT GCT TTG GAG CAG     1041
Ser Arg Gln Glu Phe Asp Val Ile Gly Thr Val Asn Ala Leu Glu Gln
            275                 280                 285

CGC CTC GAA GAT ATT ATC ACG CCG ATG GAT GTC TCT ATT ATT GGT TGT     1089
Arg Leu Glu Asp Ile Ile Thr Pro Met Asp Val Ser Ile Ile Gly Cys
290                 295                 300                 305

GTA GTG AAT GGC CCG GGT GAA GCC GAG GTT TCT ACT TTA GGT GTG GCT     1137
Val Val Asn Gly Pro Gly Glu Ala Glu Val Ser Thr Leu Gly Val Ala
            310                 315                 320

GGC GCG AAA ACC AAA AGT GGT TTC TAT GAA GAT GGC GTT CGC AAA AAA     1185
Gly Ala Lys Thr Lys Ser Gly Phe Tyr Glu Asp Gly Val Arg Lys Lys
            325                 330                 335

GAG CGT TTT GAT AAT GAC AAT ATT ATT GAT CAG CTT GAG GCG AAA ATT     1233
Glu Arg Phe Asp Asn Asp Asn Ile Ile Asp Gln Leu Glu Ala Lys Ile
            340                 345                 350

CGC GCA AAA GCA GCA ATG CTT GAT GAA ATA ACC GTA TAA AGATAAACCA      1282
Arg Ala Lys Ala Ala Met Leu Asp Glu Ile Thr Val  *
            355                 360                 365

AGTCGAAAAT AATTGTCAAA CAACTGGCTC ATTGAGGGCC AGTTTTGTTT TTATGACTTT   1342

TTG                                                                 1345

(2) INFORMATION FOR SEQ ID NO:5:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO:5:

Met His Asn Glu Ser Pro Ile Lys Arg Arg Lys Ser Thr Arg Ile Tyr
 1               5                  10                  15

Val Gly Asn Val Pro Ile Gly Asp Gly Ala Pro Ile Ala Val Gln Ser
                20                  25                  30

Met Thr Asn Thr Arg Thr Thr Asp Val Glu Ala Thr Val Arg Gln Ile
            35                  40                  45

Gln Ser Leu Glu Arg Val Gly Val Asp Ile Val Arg Val Ser Val Pro
        50                  55                  60

Thr Met Asp Ala Ala Glu Ala Phe Lys Leu Ile Lys Gln Arg Val Asn
65                  70                  75                  80

Val Pro Leu Val Ala Asp Ile His Phe Asp Tyr Arg Ile Ala Met Lys
                85                  90                  95

Val Ala Glu Tyr Gly Val Asp Cys Leu Arg Ile Asn Pro Gly Asn Ile
            100                 105                 110

Gly Ser Glu Glu Arg Ile Arg Gln Val Val Asp Ser Ala Arg His His
        115                 120                 125

Asn Ile Pro Ile Arg Ile Gly Val Asn Gly Gly Ser Leu Glu Lys Asp
        130                 135                 140

Ile Gln Glu Lys Tyr Gly Glu Pro Thr Pro Glu Ala Leu Val Glu Ser
145                 150                 155                 160
```

```
Ala Met Arg His Val Asp Ile Leu Asp Arg Leu Asn Phe Asp Gln Phe
            165                 170                 175

Lys Val Ser Val Lys Ala Ser Asp Val Phe Leu Ala Val Gly Ser Tyr
            180                 185                 190

Arg Leu Leu Ala Gln Lys Ile Asp Gln Pro Leu His Leu Gly Ile Thr
            195                 200                 205

Glu Ala Gly Gly Ala Arg Ser Gly Ser Val Lys Ser Ala Ile Gly Leu
    210                 215                 220

Gly Met Leu Leu Ala Glu Gly Ile Gly Asp Thr Leu Arg Ile Ser Leu
225                 230                 235                 240

Ala Ala Asp Pro Val Glu Glu Val Lys Val Gly Phe Asp Ile Leu Lys
                245                 250                 255

Ser Leu Arg Ile Arg Ser Arg Gly Ile Asn Phe Ile Ala Cys Pro Thr
                260                 265                 270

Cys Ser Arg Gln Glu Phe Asp Val Ile Gly Thr Val Asn Ala Leu Glu
            275                 280                 285

Gln Arg Leu Glu Asp Ile Ile Thr Pro Met Asp Val Ser Ile Ile Gly
    290                 295                 300

Cys Val Val Asn Gly Pro Gly Glu Ala Glu Val Ser Thr Leu Gly Val
305                 310                 315                 320

Ala Gly Ala Lys Thr Lys Ser Gly Phe Tyr Glu Asp Gly Val Arg Lys
                325                 330                 335

Lys Glu Arg Phe Asp Asn Asp Asn Ile Ile Asp Gln Leu Glu Ala Lys
            340                 345                 350

Ile Arg Ala Lys Ala Ala Met Leu Asp Glu Ile Thr Val
    355                 360                 365

(2) INFORMATION FOR SEQ ID NO:6:

(i) SEQUENCE CHARACTERISTICS:
        (A) LENGTH: 384 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

Met His Asn Gln Ala Pro Ile Gln Arg Arg Lys Ser Thr Arg Ile Tyr
1               5                   10                  15

Val Gly Asn Val Pro Ile Gly Asp Gly Ala Pro Ile Ala Val Gln Ser
            20                  25                  30

Met Thr Asn Thr Arg Thr Thr Asp Val Glu Ala Thr Val Phe Thr Asn
            35                  40                  45

Gln Ile Lys Ala Leu Glu Arg Val Gly Ala Asp Ile Val Arg Val Ser
    50                  55                  60

Val Pro Thr Met Asp Ala Ala Glu Ala Phe Lys Leu Ile Lys Gln Gln
65                  70                  75                  80

Val Asn Val Pro Leu Val Ala Asp Ile His Phe Asp Tyr Arg Ile Ala
                85                  90                  95

Leu Lys Val Ala Glu Tyr Gly Val Asp Cys Phe Thr Leu Arg Ile Asn
            100                 105                 110

Pro Gly Asn Ile Gly Asn Glu Glu Arg Ile Arg Met Val Val Asp Cys
            115                 120                 125

Ala Arg Asp Lys Asn Ile Pro Ile Arg Ile Gly Val Asn Ala Gly Ser
    130                 135                 140
```

```
Leu Glu Lys Asp Leu Gln Glu Lys Tyr Gly Glu Pro Thr Pro Gln Ala
145                 150                 155                 160

Leu Leu Glu Ser Ala Met Arg Phe Thr His Val Asp His Leu Asp Arg
                165                 170                 175

Leu Asn Phe Asp Gln Phe Lys Val Ser Val Lys Ala Ser Asp Val Phe
            180                 185                 190

Leu Ala Val Glu Ser Tyr Arg Leu Leu Ala Lys Gln Ile Asp Gln Pro
        195                 200                 205

Leu His Leu Gly Ile Thr Glu Ala Gly Gly Ala Arg Ser Gly Ala Val
    210                 215                 220

Lys Ser Ala Ile Phe Thr Gly Leu Gly Leu Leu Ser Glu Gly Ile
225                 230                 235                 240

Gly Asp Thr Leu Arg Val Ser Leu Ala Ala Asp Pro Val Glu Glu Ile
                245                 250                 255

Lys Val Gly Phe Asp Ile Leu Lys Ser Leu Arg Ile Arg Ser Arg Gly
            260                 265                 270

Ile Asn Phe Ile Ala Cys Pro Thr Cys Ser Arg Gln Glu Phe Asp Val
        275                 280                 285

Ile Phe Thr Gly Thr Val Asn Ala Leu Glu Gln Arg Leu Glu Asp Ile
    290                 295                 300

Ile Thr Pro Met Asp Val Ser Ile Ile Gly Cys Val Val Asn Gly Pro
305                 310                 315                 320

Gly Glu Ala Leu Val Ser Thr Leu Gly Val Thr Gly Gly Asn Lys Lys
                325                 330                 335

Ser Gly Leu Tyr Glu Asp Gly Val Arg Lys Asp Arg Leu Asp Phe Thr
            340                 345                 350

Asn Asn Asp Met Ile Asp Gln Leu Glu Ala Arg Ile Arg Ala Lys Ala
        355                 360                 365

Ser Gln Leu Asp Glu Ala Arg Arg Ile Asp Val Gln Gln Val Glu Lys
    370                 375                 380

(2) INFORMATION FOR SEQ ID NO:7:

(i) SEQUENCE CHARACTERISTICS:
        (A) LENGTH: 1079 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:7:

CAACTATTAA GCGTCGTGAA TCGACAAAAA TTTATGTGGG AAATGTACCA ATTGGTGGGG      60

ATGCGCCTAT TGCCGTGCAA TCAATGACAA ATACTCGCAC CACTGATGTG GAAGCGACAG    120

TTGCTCAAAT TAAATCATTA GAACGTGTTG GTGCAGATAT TGTTCGTGTA TCTGTTCCAA    180

CAATGGATGC TGCGGAAGCA TTTAAACAAA TTAAACAACA AGTGAATGTT CCGCTCGTAG    240

CAGATATTCA TTTCGACTAT CGTATCGCGT TAAAAGTCGC AGAATATGGA GTGGATTGTT    300

TACGTATCAA TCCTGGCAAC ATTGGTCGTG AAGATCGCGT CCGTGCCGTT GTTGATTGTG    360

CGCGAGACAA AAATATTCCG ATTCGTATTG GTGTAAATGC AGGCTCTTTA GAAAAAGATT    420

TGCAAGAAAA ATATGGCGAA CCAACGCCAG AAGCCTTGTT AGAATCCGCA TTGCGTCATG    480

TAGAAATTCT AGATCGTCTT AACTTCGATC AGTTTAAAGT GAGCGTAAAA GCCTCCGATG    540

TATTCTTAGC GGTTGAATCT TATCGTTTAC TGGCTAAAGC AATTAAACAG CCTTTACATT    600

TAGGCATTAC AGAAGCAGGT GGCGCACGCG CTGGTGCAGT AAAATCTGCA GTGGGTTTAG    660
```

```
GAATGTTATT AGCTGAGGGC ATTGGCGATA CACTACGCGT CTCTTTGGCG GCAGATCCTG      720

TAGAGGAAAT CAAAGTCGGT TTTGATATTT TGAAATCTTT ACGGATTCGT TCAAGAGGAA      780

TTAACTTTAT TGCTTGCCCA ACCTGTTCTC GCCAAGAATT TGATGTAATC GGTACAGTAA      840

ATGCGCTAGA ACAACGCCTT GAAGATATTA TTACACCAAT GGATGTATCT ATTATCGGTT      900

GTGTAGTGAA TGGTCCTGGC GAGGCACTCG TCTCCGATCT CGGCGTAACG GGCGGTAACA      960

AAAAAAGCGG TTATTATCTT GACGGAGAAC GCCAAAAAGA GCGTTTTGAT AACGAAGATA     1020

TAGTGAACCA ATTAGAAGCA AAAATTCGTG CGAAAGTCGC ACGACAAGAT CCAAAAAAC     1079

(2) INFORMATION FOR SEQ ID NO:8:

(i) SEQUENCE CHARACTERISTICS:
        (A) LENGTH: 1010 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:8:

ATGCATAACC AGGCTCCAAT TCAACGTAGA AAATCAACAC GTATTTACGT TGGGAATGTG       60

CCGATTGGCG ATGGTGCTCC CATCGCCGTA CAGTCCATGA CCAATACGCG TACGACAGAC      120

GTCGAAGCAA CGGTCAATCA AATCAAGGCG CTGGAACGCG TTGGCGCTGA TATCGTCCGT      180

GTATCCGTAC CGACGATGGA CGCGGCAGAA GCGTTCAAAC TCATCAAACA GCAGGTTAAC      240

GTGCCGCTGG TGGCTGACAT CCACTTCGAC TATCGCATTG CGCTGAAAGT AGCGGAATAC      300

GGCGTCGATT GTCTGCGTAT TAACCCTGGC AATATCGGTA ATGAAGAGCG TATTCGCATG      360

GTGGTTGACT GTGCGCGCGA TAAAAACATT CCGATCCGTA TTGGCGTTAA CGCCGGATCG      420

CTGGAAAAAG ATCTGCAAGA AAAGTATGGC GAACCGACGC CGCAGGCGTT GCTGGAATCT      480

GCCATGCGTC ATGTTGATCA TCTCGATCGC CTGAACTTCG ATCAGTTCAA AGTCAGCGTG      540

AAAGCGTCTG ACGTCTTCCT CGCTGTTGAG TCTTATCGTT TGCTGGCAAA ACAGATCGAT      600

CAGCCGTTGC ATCTGGGGAT CACCGAAGCC GGTGGTGCGC GCAGCGGGGC AGTAAAATCC      660

GCCATTGGTT TAGGTCTGCT GCTGTCTGAA GGCATCGGCG ACACGCTGCG CGTATCGCTG      720

GCGGCCGATC CGGTCGAAGA GATCAAAGTC GGTTTCGATA TTTTGAAATC GCTGCGTATC      780

CGTTCGCGAG GGATCAACTT CATCGCCTGC CCGACCTGTT CGCGTCAGGA ATTTGATGTT      840

ATCGGTACGG TTAACGCGCT GGAGCAACGC CTGGAAGATA TCATCACTCC GATGGACGTT      900

TCGATTATCG GCTGCGTGGT GAATGGCCCA GGTGAGGCGC TGGTTTCTAC ACTCGGCGTC      960

ACCGGCGGCA ACAAGAAAAG CGGCCTCTAT GAAGATGGCG TGCGCAAAGA                1010

(2) INFORMATION FOR SEQ ID NO:9:

(i) SEQUENCE CHARACTERISTICS:
        (A) LENGTH: 886 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:9:

GCGCCGGCGA TTCCGATATC AGCTTCTCTC GCTTCACCAG GTCCGTTTAC AGCGCAGCCG       60

AGAACAGCAA CTTTAATCGG CGCTTTTATC TTAGAAATAT ACTCTTCCAC TTCATTGGCA      120
```

-continued

```
ATGCTGATTA GATCAATCTC AATACGGCCG CAAGTCGGGC ATGAGATGAG CGTGGCAGCA    180

TTGGAGGCTA AGCCGAAAGA TTTCAGAAGC TCCCTTGCTA CTTTTACCTC TTCTACAGGG    240

TCTGCGCTTA GTGAAATGCG CATGGTGTTC CCGATGCCTT TGCTTAAAAT GGCGCCGAGT    300

CCTGCTGCGC TCTTTACTGT GCCGGCAAAC AGTGTTCCTG ACTCGGTGAT CCCGAGGTGA    360

AGCGGGTAGT CAAACGCTTT CGCTGCTTTT TCATAAGCCT CGATTGCAAG GTTCACGTCA    420

GAGGCCTTCA TGCTGACAAT AATATCGTGA AAATCAAGAT CCTCAAGAAT TTTAATGTGA    480

TGAAGTGCGC TTTCTACCAT TCCATCGGCA GTCGGATAAC CGTATTTTTC TAAAATCCGT    540

TTTTCCAATG AACCGGCGTT TACTCCGATT CTGATCGGAA TGCCTTTGTC TTTGGCCGCT    600

TTAACAACCG CTTCAACTTT TTCGCGCCGG CCGATATTGC CGGGGTTGAT TCGGATTTTA    660

TCTGCGCCGC CTTCAATGGC TTTCAACGCA AGTTTATAAT CGAAATGTAT GTCAACAACG    720

AGAGGAATGG AAATGCGCTT TTTAATATCC GCAATGGCGT TTGCCGCCCG TTCATCCGGA    780

CATGCTACCC GAACGATTTG GCATCCGGCT TCAGCCAAAC GGTTAATTTC CGCAACCGTT    840

GCTTCTACAT CATGTGTTTT TGTTGTTGTC ATGCTTTGGA TGACAA                  886
```

(2) INFORMATION FOR SEQ ID NO:10:

(i) SEQUENCE CHARACTERISTICS:
        (A) LENGTH: 886 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

```
GCGCCAGCCA CACCTAAAGT AGAAACCTCG GCTTCACCCG GCCATTCAC TACACAACCA     60

ATAATAGAGA CATCCATCGG CGTGATAATA TCTTCGAGGC GCTGCTCCAA AGCATTTACC    120

GTACCAATCA CATCAAATTC TTGGCGTGAA CAGGTTGGGC AAGCAATAAA GTTGATGCCA    180

CGTGAGCGGA TCCGTAACGA TTTTAGAATA TCAAAACCGA CTTTCACTTC CTCAACAGGA    240

TCTGCCGCGA GTGAGATACG TAACGTATCG CCGATACCTT CAGCCAACAA CATACCAAGA    300

CCAATTGCTG ATTTCACTGA ACCAGAACGA GCCCCACCCG CTTCTGTAAT ACCGAGGTGA    360

AGTGGTTGAT CAATTTTTTG CGCCAATAAA CGATAAGAGC CGACGGCAAG AAAGACATCC    420

GACGCTTTAA CACTGACCTT GAACTGATCG AAATTCAGCC TGTCCAAGAT ATCAACATGT    480

CGCATTGCTG ATTCAACCAA TGCTTCAGGT GTTGGCTCAC CGTATTTTTC TTGGATATCT    540

TTTTCCAGTG ACCCGCCATT GACCCCTATA CGGATAGGAA TGTTGTGATG ACGAGCACTA    600

TCAACGACTT GGCGAATACG CTCTTCACTG CCGATATTAC CTGGGTTAAT TCGTAGGCAG    660

TCAACACCAT ATTCAGCCAC TTTCATCGCG ATACGGTAGT CAAAGTGAAT ATCCGCAACC    720

AATGGCACAT TCACGCGCTG CTTAATTAAT TTAAAGGCTT CTGCTGCATC CATCGTAGGA    780

ACAGACACGC GGACGATATC AACACCTACA CGCTCAAGTG ATTGGATTTG CCGCACAGTG    840

GCTTCAACAT CCGTCGTGCG CGTATTCGTC ATAGATTGGA CAGCAA                  886
```

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:11:

```
CACTGTGCGG                                                               10
```

(2) INFORMATION FOR SEQ ID NO:12:

(i) SEQUENCE CHARACTERISTICS:
        (A) LENGTH: 1306 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 264..800

(xi) SEQUENCE DESCRIPTION: SEQ ID NO:12:

```
CTCGAGTTAA CAAGGTTGAT GTGCAAGAAG ATTTGGTATT TGTCCATGTT GGAGATAATG          60

ATTTTATTAT TTTCCCTACA CGAGTGTTTT CTTCACAAGA AGAGTTTCAG CAACTTTATT         120

CGTTTATTAA AAAGCAAATC GAGCGACATA CGGTGCCATA ATAAGCTGTT AAGTGAAGAA         180

AAGTGCACGA TTGTTTCGCT TTTTGGTGGT TCAATGGCGT TATAATGTAT CGGTATCTTT         240

AATCGACTTT AATATAGGTT TTT ATG GGC ATA GAA TAC CGC AGT CTG CAT            290
                         Met Gly Ile Glu Tyr Arg Ser Leu His
                          1               5

ACC AGC CAA TTG ACA CTG AGT GAA AAA GAA GCG CTT TAC GAT TTA TTA          338
Thr Ser Gln Leu Thr Leu Ser Glu Lys Glu Ala Leu Tyr Asp Leu Leu
 10              15                  20                  25

ATT GAA GGT TTT GAA GGC GAT TTT TCG CAT GAC GAT TTC GCG CAC ACT          386
Ile Glu Gly Phe Glu Gly Asp Phe Ser His Asp Asp Phe Ala His Thr
             30                  35                  40

TTA GGT GGA ATG CAC GTC ATG GCT TTT GAT CAA CAA AAA TTG GTT GGT          434
Leu Gly Gly Met His Val Met Ala Phe Asp Gln Gln Lys Leu Val Gly
         45                  50                  55

CAT GTT GCA ATT ATT CAA CGC CAT ATG GCC CTA GAT AAT ACG CCT ATC          482
His Val Ala Ile Ile Gln Arg His Met Ala Leu Asp Asn Thr Pro Ile
     60                  65                  70

TCT GTA GGG TAT GTT GAA GCG ATG GTA GTT GAA CAA AGT TAT CGT CGC          530
Ser Val Gly Tyr Val Glu Ala Met Val Val Glu Gln Ser Tyr Arg Arg
 75                  80                  85

CAA GGT ATT GGG CGG CAA TTG ATG CTG CAA ACC AAT AAA ATT ATA GCT          578
Gln Gly Ile Gly Arg Gln Leu Met Leu Gln Thr Asn Lys Ile Ile Ala
 90                  95                  100                 105

TCG TGT TAT CAA TTA GGG CTG CTG TCG GCT TCA GAT GAT GGA CAA AAA          626
Ser Cys Tyr Gln Leu Gly Leu Leu Ser Ala Ser Asp Asp Gly Gln Lys
             110                 115                 120

TTG TAT CAT TCG GTT GGA TGG CAA ATC TGG AAA GGT AAG TTG TTT GAA          674
Leu Tyr His Ser Val Gly Trp Gln Ile Trp Lys Gly Lys Leu Phe Glu
         125                 130                 135

TTG AAA CAA GGG AGC TAT ATC CGT TCT ATT GAA GAA GAA GGC GGA GTC          722
Leu Lys Gln Gly Ser Tyr Ile Arg Ser Ile Glu Glu Glu Gly Gly Val
     140                 145                 150

ATG GGC TGG AAA GCG GAT GGT GAG GTT GAT TTT ACC GCT TCG CTT TAC          770
Met Gly Trp Lys Ala Asp Gly Glu Val Asp Phe Thr Ala Ser Leu Tyr
 155                 160                 165

TGT GAT TTT CGT GGC GGT GAT CAG TGG TAA TCAAAATTGA ATAATATAGCG           820
Cys Asp Phe Arg Gly Gly Asp Gln Trp  *
170                 175

TTATTATTCT GGATTACTGT TAATAATATT TAGGTTAGTT TTCATTTTAT TGATAAAAAT        880
```

```
AAAACCATTA AATGGTAATC CAGTTTGACA ACAAAATTGT TATATATAGA ATACAGGCTG      940

ATTTTTAGTC TAAGGACTCG TAAGCGTTTA CGTTAATCAA CGCATATAAC TTGTCATGCA     1000

ACAGTTATAT GCTGTTGTGT TCGTCTTATT TGGAGTCTGC ACGATGTCTT CACAAAATAA     1060

AAATACCCTC TTTGGAATAC CTAAACTTCC CACCAGAGCA CTGATCTTTT TGATCCACAG     1120

GACGGGTGTG GTCGCCATGA TCGCGTAGTC GATAGTGGCT CCAAGTAGCG AAGCGAGCAG     1180

GACTGGGCGG CGGCCAAAGC GGTCGGACAG TGCTCCGAGA ACGGGTGCGC ATAGAAATTG     1240

CATCAACGCA TATAGCGCTA GCAGCACGCC ATAGTGACTG GCGATGCTGT CGGAATGGAC     1300

GATATC                                                                1306

(2) INFORMATION FOR SEQ ID NO:13:

(i) SEQUENCE CHARACTERISTICS:
        (A) LENGTH:  178 amino acids
        (B) TYPE: amino acid
        (D) TOPOLOGY: linear (ii) MOLECULE TYPE: protein (xi) SEQUENCE DESCRIPTION: SEQ ID NO:13:

Met Gly Ile Glu Tyr Arg Ser Leu His Thr Ser Gln Leu Thr Leu Ser
 1               5                  10                  15

Glu Lys Glu Ala Leu Tyr Asp Leu Leu Ile Glu Gly Phe Glu Gly Asp
                20                  25                  30

Phe Ser His Asp Asp Phe Ala His Thr Leu Gly Gly Met His Val Met
            35                  40                  45

Ala Phe Asp Gln Gln Lys Leu Val Gly His Val Ala Ile Ile Gln Arg
        50                  55                  60

His Met Ala Leu Asp Asn Thr Pro Ile Ser Val Gly Tyr Val Glu Ala
 65                  70                  75                  80

Met Val Val Glu Gln Ser Tyr Arg Arg Gln Gly Ile Gly Arg Gln Leu
                85                  90                  95

Met Leu Gln Thr Asn Lys Ile Ile Ala Ser Cys Tyr Gln Leu Gly Leu
               100                 105                 110

Leu Ser Ala Ser Asp Asp Gly Gln Lys Leu Tyr His Ser Val Gly Trp
           115                 120                 125

Gln Ile Trp Lys Gly Lys Leu Phe Glu Leu Lys Gln Gly Ser Tyr Ile
       130                 135                 140

Arg Ser Ile Glu Glu Glu Gly Gly Val Met Gly Trp Lys Ala Asp Gly
145                 150                 155                 160

Glu Val Asp Phe Thr Ala Ser Leu Tyr Cys Asp Phe Arg Gly Gly Asp
               165                 170                 175

Gln Trp
```